(12) United States Patent
Moshaverinia et al.

(10) Patent No.: US 10,907,124 B2
(45) Date of Patent: Feb. 2, 2021

(54) BIOMIMETIC MEMBRANES, METHODS OF MANUFACTURE AND USES THEREOF

(71) Applicant: The Regents of the University of California, Oakland, CA (US)

(72) Inventors: Alireza Moshaverinia, Los Angeles, CA (US); Mohammad Mahdi Hasani-Sadrabadi, Los Angeles, CA (US); Paul S. Weiss, Los Angeles, CA (US); Tara L. Aghaloo, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/264,140

(22) Filed: Jan. 31, 2019

(65) Prior Publication Data
US 2019/0276787 A1    Sep. 12, 2019

Related U.S. Application Data

(60) Provisional application No. 62/640,992, filed on Mar. 9, 2018.

(51) Int. Cl.
*C12M 1/12*      (2006.01)
*A61K 35/28*     (2015.01)
*A61L 27/54*     (2006.01)

(52) U.S. Cl.
CPC ............ *C12M 25/02* (2013.01); *A61K 35/28* (2013.01); *A61L 27/54* (2013.01); *A61L 2430/02* (2013.01); *A61L 2430/12* (2013.01); *A61L 2430/34* (2013.01); *C12N 2501/155* (2013.01); *C12N 2501/165* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 2006/0204544 A1* | 9/2006 | Sunwoo | ............... A61F 2/28 424/423 |
| 2016/0022865 A1 | 1/2016 | Francis et al. | |

FOREIGN PATENT DOCUMENTS

| | | | |
|---|---|---|---|
| WO | WO 2009/079451 | 6/2009 | |
| WO | WO-2009079451 A2 * | 6/2009 | ........... C07K 14/522 |

OTHER PUBLICATIONS

Ko, E., et al., Polydopamine-assisted osteoinductive peptide immobilization of polymer scaffolds for enhanced bone regeneration by human adipose-derived stem cells, Biomacromolecules, 14 (2013) pp. 3202-3213 (Year: 2013).*

International Search Report and Written Opinion, dated Jul. 22, 2019, from corresponding International Application No. PCT/US19/21476.

Chien et al., "Tunable Micropatterned Substrates Based on Poly(dopamine) Deposition via Microcontact Printing", Langmuir 2012, (Mar. 7, 2012), 28, 5775-5782.

(Continued)

*Primary Examiner* — Dominic Lazaro
(74) *Attorney, Agent, or Firm* — Mark S. Cohen; Pearl Cohen Zedek Latzer Baratz LLP

(57) ABSTRACT

The present invention relates to biomimetic membrane compositions and methods for making and using them.

15 Claims, 20 Drawing Sheets
Specification includes a Sequence Listing.

(56) References Cited

OTHER PUBLICATIONS

Ko et al., "Polydopamine-Assisted Osteoinductive Peptide Immobilization of Polymer Scaffolds for Enhanced Bone Regeneration by Human Adipose-Derived Stem Cells", Biomacromolecules 2013, (Aug. 13, 2013), 14, 3202-3213.

Ma et al., "Micropatterned immobilization of membrane-mimicking polymer and peptides for regulation of cell behaviors in vitro", RSC Adv., 2018 (Jun. 6, 2018), 8, 20836-20850.

* cited by examiner

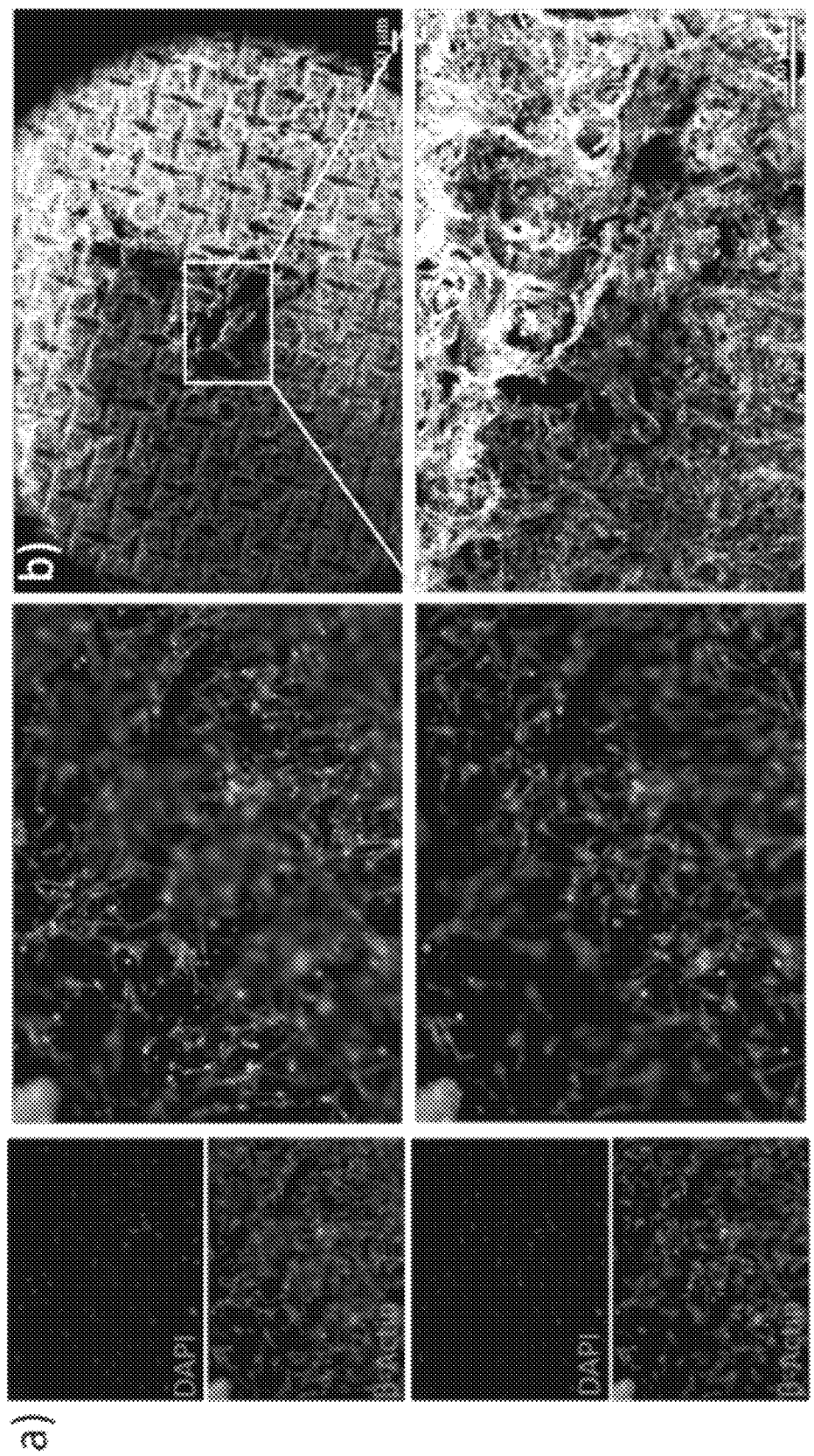

Figure 9. Immunofluorescence staining of PDLSCs on patterned membranes clearly shows the perfect covering of the structure (valleys: upper panels and heals: lower panels) with cells. β-actin (green) and DAPI (blue), scale bar: 100 μm. (b) SEM image of membranes after two weeks of culturing in regular media also confirm the ability of cells to remodel the membranes upon their movement and secreting their own extracellular matrix.

FIGURE 17
Electrospinning of PCL
(10%- HFIP, 15 kV, 10 cm)
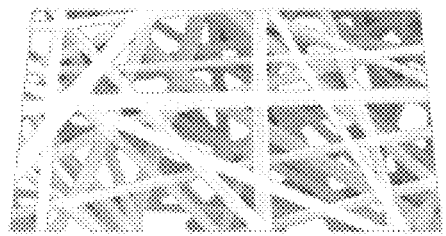
Polydopamine Coating
2 mg/ml; Tris buffer; pH 8.5; 2-16h
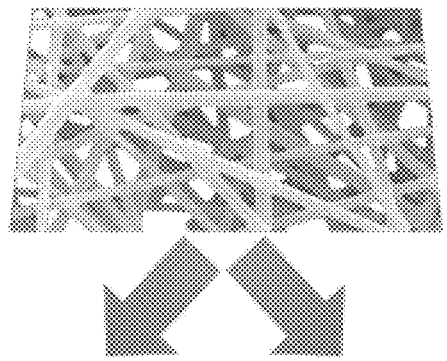
In situ mineralization
1X SBF; 1-2 weeks
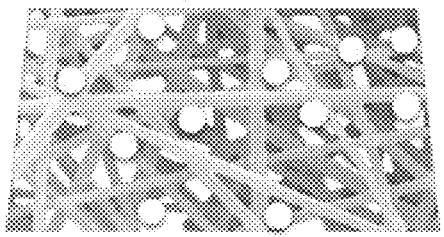
Growth Factor (BMP-2)
Loading (40-150 ng/cm$^2$)
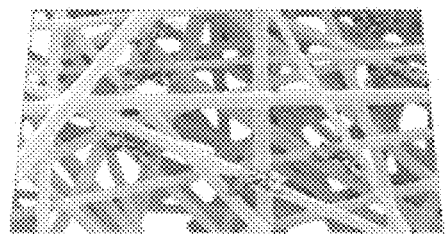

SEQUENCE LISTING

```
<160> NUMBER OF SEQ ID NOS: 8

<210> SEQ ID NO 1
<211> LENGTH: 21
<212> TYPE: DNA
<213> ORGANISM: Homo sapiens

<400> SEQUENCE: 1
cagttcccaa gcatttcatc c                                              21

<210> SEQ ID NO 2
<211> LENGTH: 20
<212> TYPE: DNA
<213> ORGANISM: Homo sapiens

<400> SEQUENCE: 2
tcaatatggt cgccaaacag                                                20

<210> SEQ ID NO 3
<211> LENGTH: 20
<212> TYPE: DNA
<213> ORGANISM: Homo sapiens

<400> SEQUENCE: 3
cgtggtgaca agggtgagac                                                20

<210> SEQ ID NO 4
<211> LENGTH: 20
<212> TYPE: DNA
<213> ORGANISM: Homo sapiens

<400> SEQUENCE: 4
taggtgatgt tctgggaggc                                                20

<210> SEQ ID NO 5
<211> LENGTH: 18
<212> TYPE: DNA
<213> ORGANISM: Homo sapiens

<400> SEQUENCE: 5
ggtgcccccg gtcttcag                                                  18

<210> SEQ ID NO 6
<211> LENGTH: 23
<212> TYPE: DNA
<213> ORGANISM: Homo sapiens

<400> SEQUENCE: 6
agggccaggg ggtccagcat ttc                                            23

<210> SEQ ID NO 7
<211> LENGTH: 21
<212> TYPE: DNA
```

```
<213> ORGANISM: Homo sapiens

<400> SEQUENCE: 7
agccgcatct tcttttgcgt c                                              21

<210> SEQ ID NO 8
<211> LENGTH: 21
<212> TYPE: DNA
<213> ORGANISM: Homo sapiens

<400> SEQUENCE: 8
tcatatttgg caggttttc t                                               21
```

BIOMIMETIC MEMBRANES, METHODS OF MANUFACTURE AND USES THEREOF

CROSS REFERENCE TO RELATED APPLICATIONS

This application claims the benefit of U.S. Provisional Application No. 62/640,992, filed Mar. 9, 2018, which is incorporated by reference herein in its entirety.

GOVERNMENT INTEREST STATEMENT

This invention was made with government support under Grant Number DE023825, awarded by the National Institutes of Health. The government has certain rights in the invention.

FIELD OF THE INVENTION

The present invention relates to biomimetic membrane compositions and methods for making and using them.

BACKGROUND OF THE INVENTION

Periodontal disease is a chronic destructive inflammatory disease which is one of the most prevalent chronic dental infections in humans. Periodontitis, the more serious form of the disease, leads to the destruction of the periodontium, which is a set of specialized tissues that support the teeth, alveolar bone, periodontal ligaments (PDL), and root cementum. If left untreated, periodontitis results in progressive loss of periodontal attachment and surrounding bone loss that may lead to early tooth loss. The ultimate goal of periodontal therapy is the regeneration of all components of the periodontium. Currently, no ideal treatment for periodontitis is available.

The use of mesenchymal stem cells (MSCs) presents an advantageous therapeutic option for periodontal tissue engineering. Gingival mesenchymal stem cells (GMSCs) are of special interest as they are easily accessible in the oral cavity and readily found in discarded dental tissue samples. Biomaterials have been widely used as cell delivery vehicles to direct stem cell differentiation toward desired phenotypes. In vitro, cultures of micron-scale cell aggregates recreate the biochemical and biophysical microenvironment of native tissues defined by cell-cell communications. Adhesion and retention of the biomaterial at the application site as well as its regenerative properties are vital factors for successful periodontal tissue regeneration. However, the major drawbacks of the current cell-laden biomaterials for periodontal tissue engineering are weak adhesion to the tissue, poor mechanical strength, fast/uncontrolled degradation, and absence of regenerative properties. Collagen has been used for periodontal tissue repair; however, poor mechanical properties, fast degradation in vivo, and difficulty keeping the material at the site are some of its major drawbacks. Teflon is mechanically strong but needs removal which can cause recontamination of bone growth site. Other membranes are known as well. Most of these are non-absorbable, including Millipore® filter, Teflon, and titanium-reinforced expanded polytetrafluoroethylene membranes. The main disadvantage of these membranes is the need for a second surgical operation to remove them. A high chance of infection has been reported with such non-absorbable membranes.

There are also few biodegradable membranes (mainly based on collagen) that can be used as an alternative for periodontal restoration. Degradation of such a membrane would eliminate the second surgery which will be quite beneficial to the patient and surgeon. Most of the commercially available collagen membranes have been developed from type I collagen, a predominant component of periodontal connective tissue, or from a combination of type I and type III collagen. However, there are issues with lack of appropriate mechanical properties and the fast rate of membrane degradation, which can also be influenced by factors such as the local pH and membrane composition. Thus, these collagen membranes exhibit variable degradation times in use and there is the concern for an immunological response to a foreign protein with this material.

Other known membranes include polygalactin (Vicryl®) mesh and a polylactic acid membrane. However, precise placement of the membranes at the treatment site can be difficult due to their non-adherent nature, thereby lengthening the surgical procedure and adding unpredictability to the therapeutic outputs.

Moreover, conventional periodontal membranes lack osteoconductivity, osteodifferentiation, and regenerative properties. Adhesive biomaterials (e.g., fibrin glue) are not promising cell delivery vehicles for periodontal tissue repair due to their lack of regenerative properties. Currently, there is no single biomaterial that combines the above-mentioned desired properties. Accordingly, there is a need for improved materials and methods that combine the above-mentioned desirable properties and that can be used to facilitate tissue engineering, such as periodontal tissue regeneration.

SUMMARY OF THE INVENTION

In an embodiment, provided herein is a biomimetic composition comprising: a fibrous membrane comprising: a synthetic polymer; a coating comprising polydopamine disposed on said synthetic polymer; and a stromal cell-derived factor 1 (SDF-1α) disposed on the coating. In one embodiment, the membrane is patterned with niches. In one embodiment, the synthetic polymer comprises poly(ε-caprolactone) (PCL). In one embodiment niches comprise a pattern configured to facilitate adhesion of stem cells to the membrane.

In one embodiment, the composition further comprises an additional stem cell attractant, which may be a growth factor such as a bone morphogenetic growth factor, a vascular endothelial growth factor or any combination thereof. In one embodiment, the composition may further comprise a gelatin protein disposed on the membrane. In one embodiment, the ratio of gelatin protein to the synthetic polymer is in a range of about 1:1 to about 1:4.

In another embodiment, provided herein is a method of promoting periodontal tissue regeneration in a subject, said method comprising: positioning a biomimetic composition between a gum and a root surface of a tooth in the subject, the composition comprising: a fibrous membrane comprising: a synthetic polymer; a coating comprising polydopamine disposed on the synthetic polymer; and a stromal cell-derived factor 1 (SDF-1α) disposed on the coating, thereby promoting periodontal tissue regeneration in the subject. In one embodiment, the membrane is patterned with niches. In one embodiment, the synthetic polymer comprises poly(ε-caprolactone) (PCL). In one embodiment niches comprise a pattern configured to facilitate adhesion of stem cells to the membrane.

In one embodiment, the method provides a composition further comprising an additional stem cell attractant, which may be a growth factor such as a bone morphogenetic growth factor, a vascular endothelial growth factor or any combination thereof. In one embodiment, the method provides a composition further comprising a gelatin protein disposed on the membrane. In one embodiment, the ratio of gelatin protein to the synthetic polymer is in a range of about 1:1 to about 1:4.

In another embodiment, provided herein is a process for preparing a biomimetic composition, said process comprising: depositing a synthetic polymer on a substrate; depositing a coating comprising polydopamine on the synthetic polymer; and depositing a stromal cell-derived factor 1 (SDF-1α) on the coating. In one embodiment of the process, depositing the synthetic polymer comprises electrospinning. In one embodiment, the deposited synthetic polymer comprises fibers formed into a fibrous membrane. In one embodiment of the process, micropatterning niches are provided on a surface of the synthetic polymer.

In one embodiment of the process, the micropatterning comprises molecular ultraviolet (UV)-based photopatterning, microcontact printing, or morphological micropatterning. In one embodiment, the synthetic polymer comprises PCL. In one embodiment of the process, an additional stem cell attractant is deposited on the coating, such as a growth factor, which may be a bone morphogenetic growth factor, a vascular endothelial growth factor, or any combination thereof. In one embodiment of the process, gelatin protein may be disposed on the membrane. In one embodiment, the ratio of gelatin protein to the synthetic polymer is in a range of about 1:1 to about 1:4.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 9 (a) Immunofluorescence staining of PDLSCs on patterned membranes clearly shows the perfect covering of the structure (valleys: upper panels and heals: lower panels) with cells. β-actin (green) and DAPI (blue), scale bar: 100 μm. (b) SEM image of membranes after two weeks of culturing in regular media also confirm the ability of cells to remodel the membranes upon their movement and secreting their own extracellular matrix.

FIG. 17. Schematic representation of PDA-PCL modification with simulated body fluid and rhBMP-2 before culturing the stem cells.

DETAILED DESCRIPTION OF THE PRESENT INVENTION

Figure 1:
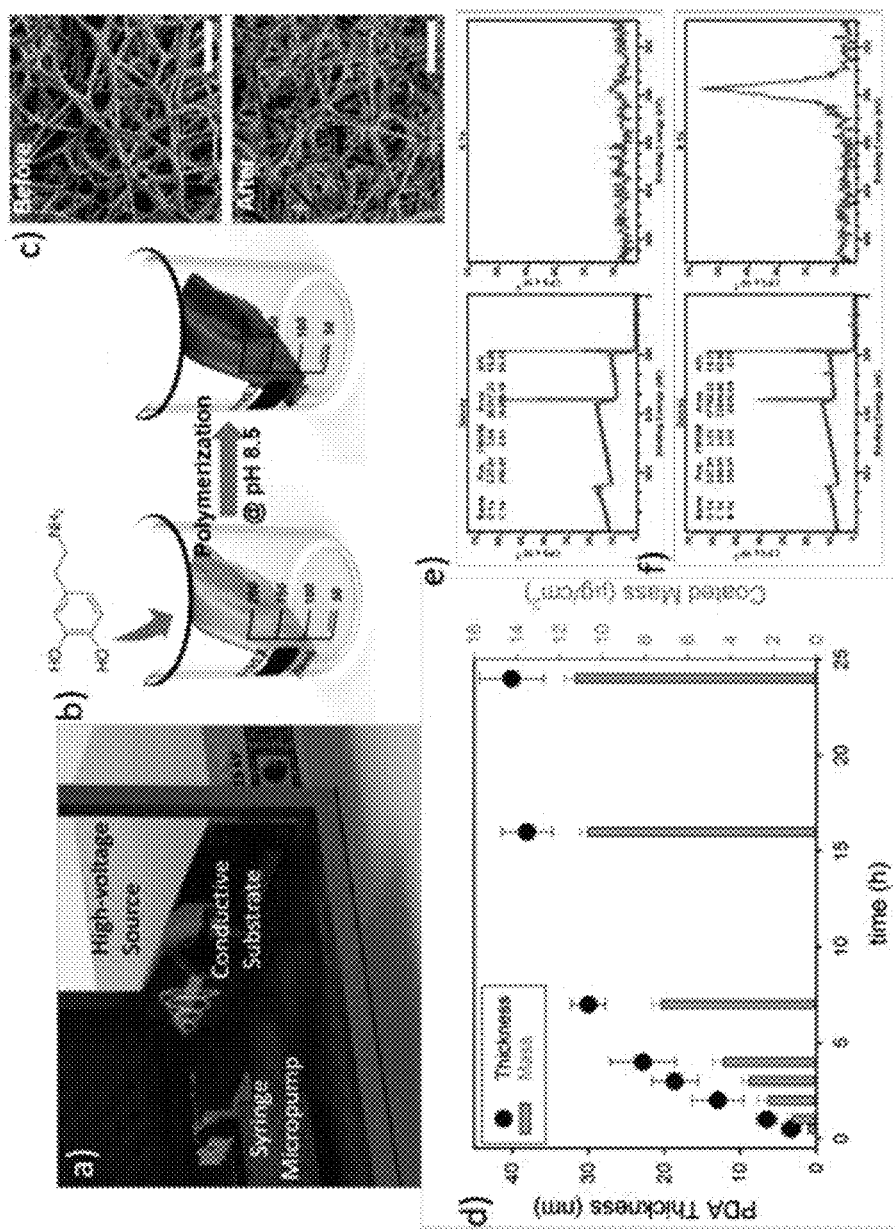
FIG. 1. (a) Schematic of electrospinning process used to make a membrane in accordance with embodiments described herein. Solution of FDA-approved poly(ε-caprolactone) (PCL) (10% in HFIP) electrospun at 15 kV with tip-to-target distance of 10 cm and constant infusion rate of 2.5 ml/h for a total of 0.5 ml per membrane. (b) Schematic overview of self-polymerization reaction implemented to coat PCL membrane with polydopamine (PDA). (c) Scanning electron microscopy (SEM) images of prepared nanofibers before (top) and after (bottom) PDA deposition. (d) Relationship between time of polymerization and deposition thickness as well as density of deposited PDA. The presented data are expressed as average±SD. Surface chemical composition of nanofibers as investigated by XPS spectra for PCL (e) and PDA-PCL (f). High-resolution spectra of nitrogen peaks (N1s) for PCL and PDA-coated PDA also presented at right.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or preferably within ±10% of the stated amount, or more preferably within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

As used herein, the terms "component," "composition," "formulation", "composition of compounds," "compound," "drug," "pharmacologically active agent," "active agent," "therapeutic," "therapy," "treatment," or "medicament," are used interchangeably herein, as context dictates, to refer to a compound or compounds or composition of matter which, when administered to a subject (human or animal) induces a desired pharmacological and/or physiologic effect by local and/or systemic action. A personalized composition or method refers to a product or use of the product in a regimen tailored or individualized to meet specific needs identified or contemplated in the subject.

The terms "subject," "individual," and "patient" are used interchangeably herein, and refer to an animal, for example a human, to whom treatment with a composition or formulation in accordance with the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment, the human is a child. The human can be male, female, pregnant, middle-aged, adolescent, or elderly. According to any of the methods of the present invention and in one embodiment, the subject is human In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

To address, inter alia, limitations observed with conventional biomaterials used in applications such as periodontal tissue engineering, the present invention reflects efforts to combine multiple physiochemical techniques to expand the features and achieve new types of membranes.

In an embodiment, the present disclosure describes herein, inter alia, the first barrier membrane for tissue regeneration comprising a totally synthetic biodegradable material that adheres to the repair site after placement to form a membrane having the precise geometry needed for that location and the optimum porosity to prevent epithelial tissue downgrowth. As described herein, various microtechnologies have been implemented to control localization of preferred stem cells which can be attributed to differentiation of cultured cells. The micropatterned membranes described in embodiments herein can also handle three-dimensional stem cell aggregates and control their fate which can be crucial to achieving strong therapeutic outcome. Embodiments of the present invention have been shown to exhibit a surprising and unexpected combination of the following properties: (1) osteo-differentiation; (2) suitable mechanical characteristics to ensure the proliferation and infiltration of stem cells and desirable tissue formation; (3) fluorescence; (4) strong adhesion to surrounding tissues; (4) biodegradability with degradation rate relative to tissue ingrowth; and (5) high in vivo biocompatibility. Thus, membranes can be designed to achieve prolonged degradation (increasing the chances of full recovery), enhanced mechanical properties (reducing the risk of failure), enhanced mineralization (for faster recovery), enhanced adhesion (for easier placement), at a significantly reduced, more affordable price.

Membranes in accordance with embodiments described herein can be used to treat periodontitis and also, inter alia, as a dental membrane in the bone graft substitutes market. Approximately 64.7 million Americans have periodontitis and the dental membrane and bone graft substitutes market is expected to rise to $922.6 million in 2024. However, as described herein, membranes can be designed to tune differentiation of stem cells for in situ recruitment and controlled differentiation of stem cells for other tissue targets as well.

In an aspect, the present invention relates to membranes that are biodegradable and nontoxic, and intended for personalized tissue regeneration. As discussed in detail herein, in order to, inter alia, address the clinical need for adhesive biomaterials for tissue regeneration, a new biomimetic biomaterial was engineered with tunable physical properties and the ability to directly encapsulate stem cells and regulate their differentiation toward specific tissues (e.g., osteogenic or periodontal ligament-like tissues).

An embodiment in accordance with the membranes described herein is made of FDA-approved synthetic polymer, poly (ε-caprolactone) (PCL) coated with polydopamine In one exemplary manufacturing technique, the PCL is first electrospun and then the polydopamine coated in a biomimetic fashion so that the coating is a mimic of mussel adhesive proteins that contain 3,4-dihydroxy-L-phenylalanine (DOPA). In embodiments, the polydopamine coating accelerates the mineral deposition of hydroxyapatite in the presence of simulated body fluids or saliva (which can accelerate osteogenic differentiation of cultured stem cells). The polydopamine surprisingly can also be tuned as described herein to exhibit fluorescence that can be used to diagnose the health of the tissue while the membrane is being used.

Membranes in accordance with embodiments described herein also exhibit surface adsorption and release of several growth factors (GFs). The GFs attract stem cells from the in vivo environment in which the membrane is placed, so as to selectively promote growth of bone tissue and/or periodontal ligament tissue. As demonstrated by the Examples provided herein, functionality of the novel membrane was confirmed with several types of dental-derived human mesenchymal stem cells, including gingival-derived mesenchymal stem cell (GMSCs), human periodontal ligament stem cells (PDLSCs), Dental pulp stem cells (DPSCs), stem cells from human exfoliated deciduous teeth (SHED), and human bone-marrow mesenchymal stem cells, (hBMMSCs). Culturing these stem cells on the developed membrane could regulate the stem cells' fate and push them to differentiate to bone cells (osteoblast) in about 2-4 weeks.

Membranes in accordance with embodiments described herein have been micropatterned and tested with multiscale architecture to enhance periodontal tissue regeneration. Multiple molecular UV-based photopatterning and microcontact printing, and morphological micropatterning approaches have been developed to control localization and fate of stem cells. As described and illustrated herein, the membrane not only recruits the stem cells but also pushes the stem calls towards mineralized tissue as confirmed by molecular, chemical and immunohistochemical techniques. In embodiments, designated micropatterns mimic the homing features of cellular niches and can hold cell aggregates as desired. This fibrous niche can provide physical support and offer a way to easily culture, handle, and implant cell aggregates.

In one or more embodiments, the structures are also modified by short peptides or extracellular proteins at cell adhesion sites. It was contemplated that this would manipulate the chemical features of the substrate in accordance with physical patterns in order to regenerate heterogenous tissues. Degradation and mechanical properties of the membranes were also tuned by adding gelatin protein to the formulation in different compositions. Therefore, fibrous membranes can provide the stiffness similar to the native cellular microenvironment.

In one or more embodiments, application of the membrane is suitable for periodontal tissue regeneration and personalized precision oral care. A periodontal membrane can guide tissue regeneration that regenerates periodontium (e.g. periodontal ligament and alveolar bone). The periodontal membrane can act as a mechanical barrier that prevents and/or retards the apical migration of the gingival epithelium and allows periodontal ligament and bone tissues to selectively repopulate the root surface during healing.

In one embodiment, provided herein is a biomimetic composition comprising a fibrous membrane comprising a synthetic polymer; a coating comprising polydopamine disposed on said synthetic polymer; and a stromal cell-derived factor 1 (SDF-1α) disposed on the coating. In an embodiment, the membrane is patterned with niches. In another embodiment, the synthetic polymer comprises poly(ε-caprolactone) (PCL). In an embodiment, the synthetic polymer has a molecular weight in the range from about 10 kDa to about 100 kDa. In an embodiment, the synthetic polymer has a molecular weight in the range from about 55 kDa to about 86 kDa. In an embodiment, the synthetic polymer has a molecular weight of about 80 kDa. In an embodiment, the synthetic polymer comprises PCL having a molecular weight of 80 kDa. Any other synthetic polymer suitable for use in accordance with the compositions and methods described herein can be used. Such materials are within the knowledge and understanding of the ordinarily skilled artisan and can include, without limitation, poly lactide (PLA), polyethylene oxide (PEO), poly-(lactide-co-glycolide) (PLGA), collagen, polyethylene, polytetrafluoroethylene (PTFE), or poly(ethylene glycol)-poly(lactic acid) or any other suitable material. In another embodiment, the niches comprise a pattern configured to facilitate adhesion of stem cells to the membrane. Niches as described in accordance with embodiments herein can be any shape or configuration suitable to achieve the desired result. In embodiments, the niches can have different shapes and sizes. In embodiments relating to applications in dentistry, the niches can be square shaped. In an embodiment, the niches have a width of between about 50 and about 700 micrometers and/or a depth of between about 10 and about 100 micrometers.

In an embodiment, the composition further comprises an additional stem cell attractant. In another embodiment, the additional stem cell attractant comprises a growth factor. In another embodiment, the growth factor comprises a bone morphogenetic growth factor, a vascular endothelial growth factor or combination thereof. In embodiments of the compositions, methods, and processes described herein, other suitable growth factors can be used alone or in combination, including, without limitation, fibroblast growth factors (FGFs), platelet derived growth factors (PDGFs), Insulin-like growth factors, or any other growth factor suitable for achieving the desired result or results as described herein.

In an embodiment, the composition further comprises a gelatin protein disposed on the membrane. In an embodiment, the ratio of gelatin protein to the synthetic polymer is in a range of about 1:1 to about 1:4. In an embodiment, the ratio of gelatin protein to synthetic polymer is about 1:3. In an embodiment, the ratio of gelatin protein to synthetic polymer is about 1:4. In an embodiment, the ratio of gelatin protein to synthetic polymer is 1:4.

In another embodiment, provided herein is a method of promoting periodontal tissue regeneration in a subject, the method comprising positioning a biomimetic composition between a gum and a root surface of a tooth in the subject, the composition comprising a fibrous membrane comprising a synthetic polymer; a coating comprising polydopamine disposed on the synthetic polymer; and a stromal cell-derived factor 1 (SDF-1α) disposed on the coating, thereby promoting periodontal tissue regeneration in the subject. In an embodiment, the membrane is patterned with niches, as described herein. In another embodiment, the synthetic polymer comprises poly(ε-caprolactone) (PCL). In another embodiment, the niches comprise a pattern configured to facilitate adhesion of stem cells to the membrane.

In another embodiment, the composition further comprises an additional stem cell attractant, as described herein. In another embodiment, the additional stem cell attractant comprises a growth factor. In another embodiment, the growth factor comprises a bone morphogenetic growth factor, a vascular endothelial growth factor, or combination thereof.

In an embodiment, the method further comprises a gelatin protein disposed on the membrane. In an embodiment, the ratio of gelatin protein to the synthetic polymer is in a range of about 1:1 to about 1:4. In an embodiment, the ratio of gelatin protein to synthetic polymer is about 1:3. In an embodiment, the ratio of gelatin protein to synthetic polymer is about 1:4. In an embodiment, the ratio of gelatin protein to synthetic polymer is 1:4.

In an embodiment, the periodontal tissue comprises bone tissue, ligament tissue, or a combination thereof.

In another embodiment, provided herein is a process for preparing a biomimetic composition, the process comprising: depositing a synthetic polymer on a substrate; depositing a coating comprising polydopamine on the synthetic polymer; and depositing a stem cell attractant on the coating. In an embodiment, the stem cell attractant is a stromal cell-derived factor 1 (SDF-1α).

In another embodiment, provided herein is a process for preparing a biomimetic composition, the process comprising: depositing a synthetic polymer on a substrate; depositing a coating comprising polydopamine on the synthetic polymer; and depositing a stromal cell-derived factor 1 (SDF-1α) on the coating. In an embodiment, depositing the synthetic polymer comprises electrospinning Any other suitable process for depositing a synthetic polymer in accordance with processes and compositions described herein can be used, including, without limitation, sol-gel technique or plasma spraying.

In an embodiment, the substrate is a metallic substrate. In an embodiment, the substrate comprises stainless steel. Any other substrate suitable for receiving a deposited polymer in accordance with embodiments described herein can be employed.

In an embodiment, the deposited synthetic polymer comprises fibers formed into a fibrous membrane. In embodiments of the compositions described herein, the fibrous membrane comprises fibers having a length and/or diameter in a range of about 100 to about 2500 nanometers. In embodiments, the compositions further comprise an extracellular matrix secreted by the stem cells and that remodels the fibrous membrane.

In an embodiment, the process further comprises micropatterning niches, as described herein, on a surface of the synthetic polymer. In an embodiment, the micropatterning comprises molecular ultraviolet (UV)-based photopatterning, microcontact printing, or morphological micropatterning.

In an embodiment, the synthetic polymer comprises PCL. In an embodiment, the process further comprises depositing an additional stem cell attractant on the coating. In another embodiment, the additional stem cell attractant comprises a growth factor. In an embodiment, the growth factor comprises a bone morphogenetic growth factor, a vascular endothelial growth factor, or combination thereof.

In another embodiment, the process further comprises a gelatin protein disposed on the membrane. In an embodiment, the ratio of gelatin protein to the synthetic polymer is in a range of about 1:1 to about 1:4. In an embodiment, the ratio of gelatin protein to synthetic polymer is about 1:3. In an embodiment, the ratio of gelatin protein to synthetic polymer is about 1:4. In an embodiment, the ratio of gelatin protein to synthetic polymer is 1:4.

In an embodiment, provided herein is a biomimetic composition comprising: a fibrous membrane patterned with niches, the membrane comprising: a synthetic polymer; and a coating comprising polydopamine disposed on said synthetic polymer.

In another embodiment, provided herein is a biomimetic composition comprising: a fibrous membrane patterned with niches, the membrane comprising a synthetic polymer; a coating comprising polydopamine disposed on said synthetic polymer; and at least one stem cell attractant disposed on the coating.

In an embodiment, the synthetic polymer comprises poly (ε-caprolactone) (PCL). In another embodiment, the niches comprise a pattern configured to facilitate adhesion of stem cells to the membrane. In an embodiment, the stem cell attractant comprises a growth factor. In an embodiment, the growth factor comprises a cytokine. In another embodiment, the cytokine comprises a chemokine. In another embodiment, the chemokine comprises stromal cell-derived factor 1 (SDF-1α). Any other suitable stem cell attractant for achieving the desired results can be used in accordance with the compositions, methods, and processes described herein, including, for example, without limitation, a CXCR4 antagonist.

In an embodiment, the composition further comprises a bone morphogenetic growth factor or a vascular endothelial growth factor or combination thereof. In another embodiment, the composition further comprises a gelatin protein disposed on the membrane. In another embodiment, the ratio of gelatin protein to the synthetic polymer is in a range of about 1:1 to about 1:4. In an embodiment, the ratio of gelatin protein to synthetic polymer is about 1:3. In an embodiment, the ratio of gelatin protein to synthetic polymer is about 1:4. In an embodiment, the ratio of gelatin protein to synthetic polymer is 1:4.

In another embodiment, provided herein is a method of promoting periodontal tissue regeneration in a subject, the method comprising positioning a biomimetic composition described herein between a gum and a root surface of a tooth in the subject, thereby promoting periodontal tissue regeneration in the subject. In an embodiment, the periodontal tissue comprises bone tissue or ligament tissue or a combination thereof.

In an embodiment, provided herein is a process for preparing a biomimetic composition as described herein, said process comprising depositing a synthetic polymer on a substrate; micropatterning niches on a surface of the synthetic polymer; and depositing a coating comprising polydopamine on the synthetic polymer. In an embodiment, the depositing comprises electrospinning.

In an embodiment, the deposited synthetic polymer comprises fibers formed into a fibrous membrane. In an embodiment, the micropatterning comprises molecular ultraviolet (UV)-based photopatterning, microcontact printing, or morphological micropatterning.

In an embodiment, provided herein is a system comprising biomimetic compositions as described herein, wherein the polydopamine emits fluorescence when a source of electromagnetic radiation is coupled to the polydopamine, an intensity of the fluorescence changes depending on a pH of the in vivo environment, the pH that is neutral indicates the in vivo environment is healthy, and the pH that is acidic indicates the in vivo environment comprises inflammation.

In an embodiment, a composition in accordance with those described herein further comprises a gelatin protein coupled to the fibrous membrane, wherein a composition of the gelatin protein: tunes degradation and mechanical strength of the membrane, and controls release of therapeutic proteins from the fibrous membrane. In an embodiment, a ratio of the gelatin protein to the poly(ε-caprolactone) in the fibrous membrane is in a range of about 1:1 to about 1:4 so that the fibrous membrane: degrades in the vivo environment after a time in a range of about 4-6 months; exhibits a Young's modulus in a range of about 1-10 MPa; and/or exhibits a tensile strength in a range of about 1-4 MPa.

In an embodiment, in a composition as described herein, the fibrous membrane accelerates mineral deposition of hydroxyapatite in a presence of saliva in the in vivo environment. In an embodiment, the polydopamine adheres to the root surface in a presence of saliva in the environment. In an embodiment, the composition is a bone graft material.

In an embodiment, provided herein is a method of making a tissue regeneration composition, comprising: depositing a fibrous membrane including a synthetic polymer on a substrate; patterning niches in the fibrous membrane using a mold or photolithography; depositing a coating comprising polydopamine on the synthetic polymer; and depositing stromal cell-derived factor 1 (SDF-1α) cytokine, recombinant human bone morphogenetic proteins-2 (rhBMP-2) growth factor, and/or Vascular endothelial growth factor (VEGF) on the polydopamine, wherein: the SDF cytokine is released from the fibrous membrane over time and attracts stem cells from an in vivo environment in which the fibrous membrane is placed, the fibrous membrane suppresses epithelial tissue growth from the in vivo environment; and the niches collect the stem cells so as to selectively promote growth of bone tissue and/or periodontal ligament tissue in the in vivo environment.

In an embodiment, provided herein is a method of growing periodontal tissue, comprising: depositing a membrane composition in an in vivo environment between gum and a root surface of a tooth, the membrane composition patterned with niches and including: (a) a synthetic polymer; (b) a coating comprising polydopamine on the synthetic polymer; (c) stromal cell-derived factor 1 (SDF-1α) cytokine, recombinant human bone morphogenetic proteins-2 (rhBMP-2) growth factor, and Vascular endothelial growth factor (VEGF) on the polydopamine; wherein the components (a)-(c) are disposed in the membrane composition such that: the SDF growth factor is released from the membrane composition over time and attracts stem cells from an in vivo environment in which the membrane composition is placed, the membrane composition suppresses epithelial tissue growth from the in vivo environment; and the niches collect the stem cells so as to selectively promote growth of bone tissue and/or periodontal ligament tissue in the in vivo environment.

In an embodiment, a method as described herein further comprises irradiating the membrane composition with electromagnetic radiation, wherein: the polydopamine emits fluorescence in response to the electromagnetic radiation, an intensity of the fluorescence changes depending on a pH of the in vivo environment, the pH that is neutral indicates the in vivo environment is healthy, and the pH that is acidic indicates the in vivo environment has inflammation.

In an embodiment, the stem cells exhibit more than 60% in vitro differentiation when disposed on the membrane composition.

In another embodiment, provided is a composition comprising a fibrous membrane patterned with niches, comprising a synthetic polymer and a coating comprising polydopamine on the synthetic polymer.

All patents, patent applications, and scientific publications cited herein are hereby incorporated by reference in their entirety.

The following examples are presented in order to more fully illustrate the preferred embodiments of the invention. It should in no way be construed, however, as limiting the broad scope of the invention.

EXAMPLES

A series of membranes with a tunable biomimetic coating layer were fabricated to control deposition, culturing, and differentiation of dental derived stem cells. Degradation rate, mechanical properties, and release of desired therapeutic proteins were also controlled.

Example 1

Figure 5:
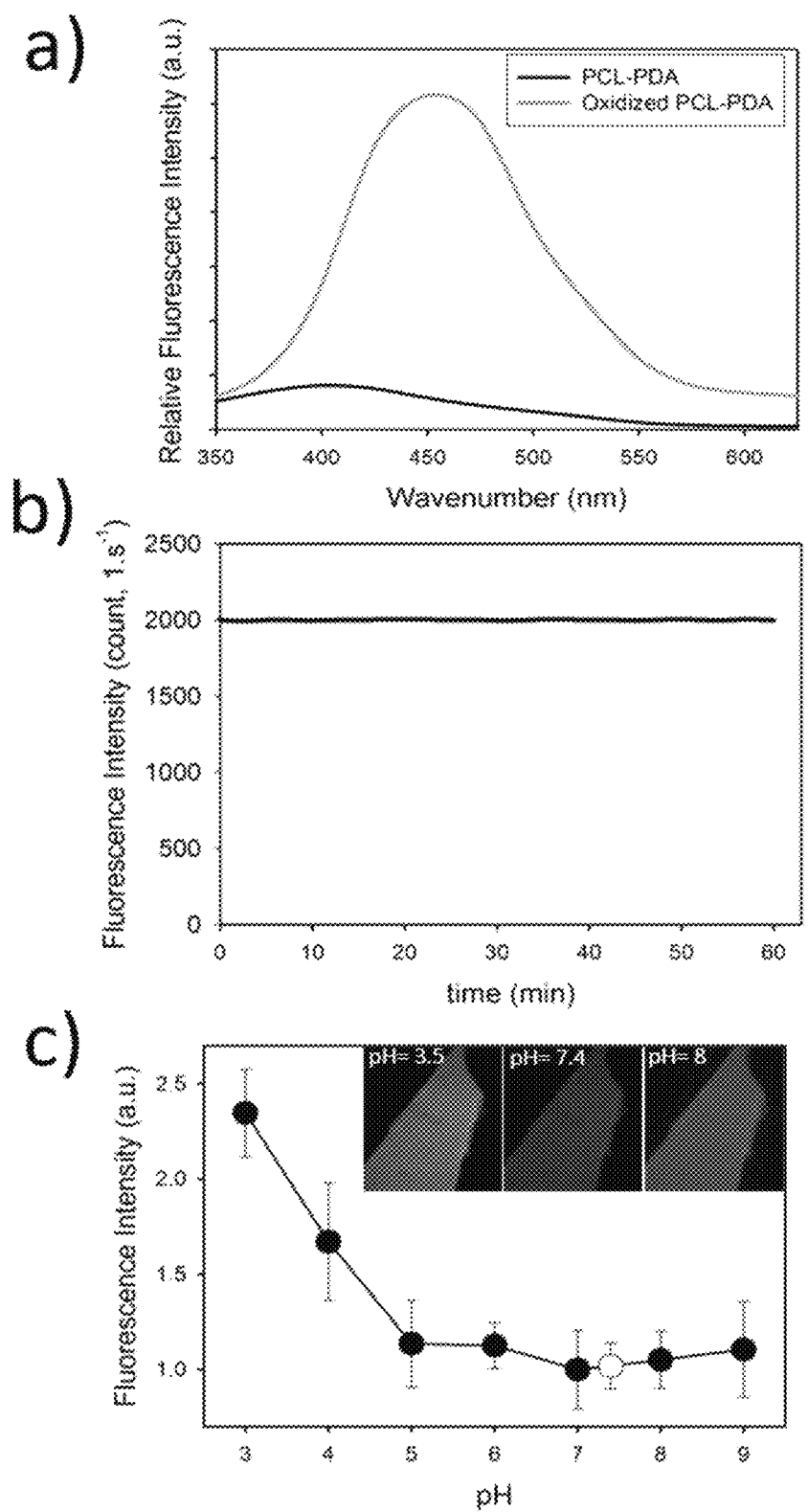
FIG. 5. (a) Relative fluorescence emission spectra of oxidized PCL-PDA membrane as prepared by performing the deposition reaction in an oxidative environment. (b) Emission intensity of oxidized PCL-PDA membrane during continuous excitation. (c) pH dependency of fluorescence intensity at constant excitation of 405 nm.
Figure 6:
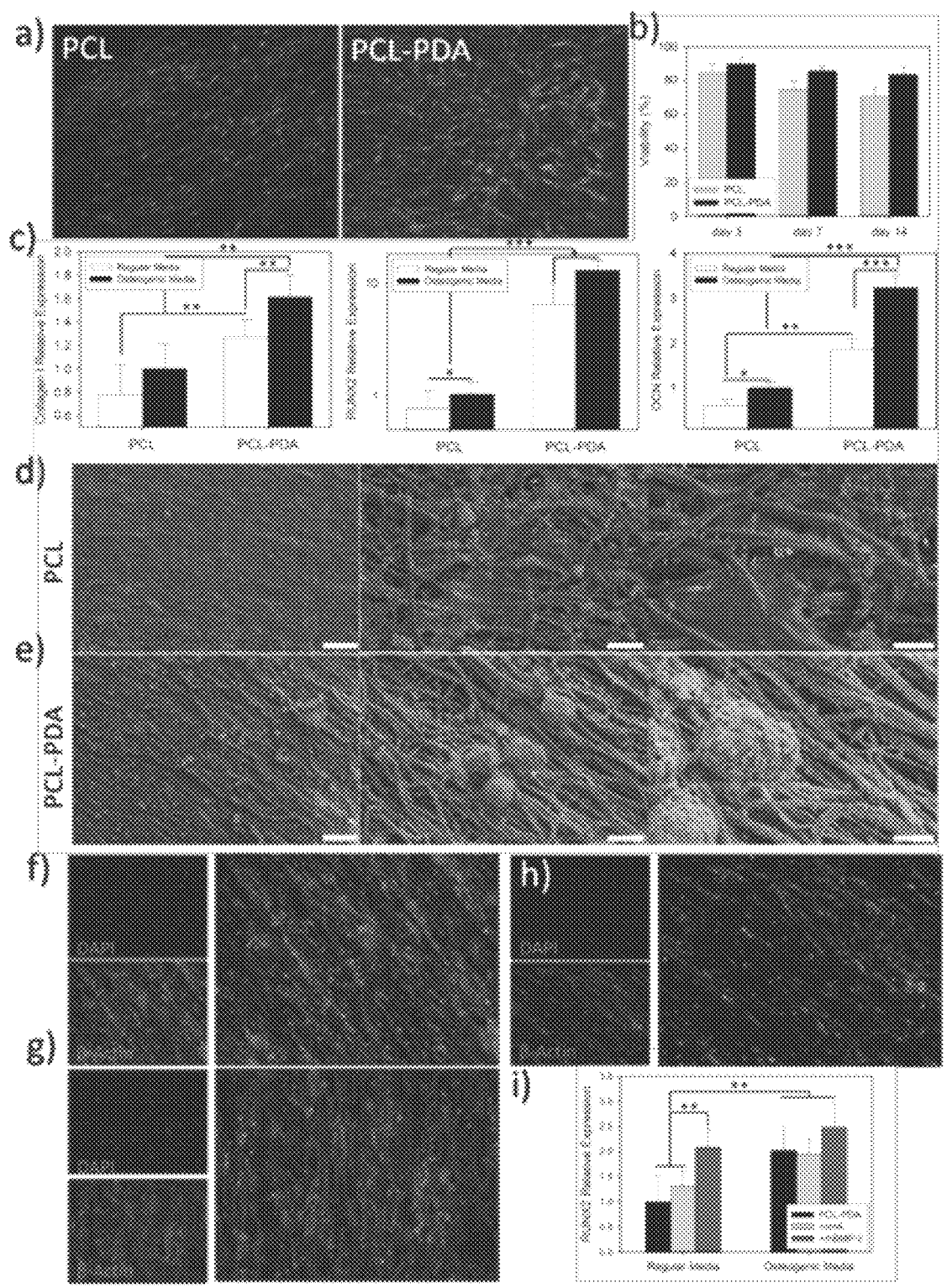
FIG. 6. (a) Viability of periodontal ligament stem cells (PDLSCs) cultured on the PCL (left) and PCL-PDA (right) electrospun membranes was checked using Live/Dead fluorescence assay at different time points (b). (c) Gene expression analysis of osteogenic markers. Real time PCR analysis of the osteo-differentiation of PDSCs cultured on PCL and on PCL-PDA membranes after four weeks of culturing in regular or osteogenic media. Expression of three osteogenes, Col1, RUNX2, and OCN, was evaluated with reference to the housekeeping gene GAPDH. Data are expressed as average±SD. The results were statistically analyzed using unpaired t-tests, n=3. For all the tests, the threshold was set to $p<0.01$ for "statistically very significant" and $p<0.001$ for "statistically extremely significant." Statistical significance is indicated by  (very significant) and * (extremely significant) for indicated comparisons. Morphology of PDSCs cultured on PCL (d) and PCL-PDA (e) membranes after four weeks of culturing in osteogenic media evaluated by SEM and presented at different magnifications; scale bars represent 200, 20, 2 μm, left to right Immunofluorescence staining of PDLSCs on membranes with different formulations after two weeks of culturing in regular media. (f) PCL-PDA membranes, (g) PCL-PDA membranes pre-treated in artificial saliva for 48 h before adding stem cells, (h) PCL-PDA membranes, pre-treated with rhBMP-2 growth factor (100 ng/ml). β-actin (green) and DAPI (blue), scale bar: 100 μm. (i) real-time PCR analysis of osteogenic gene RUNX2, with reference to the housekeeping gene GAPDH for PDSCs cultured on PCL-PDA with or without pre-treatment in artificial saliva or with rhBMP-2 after four weeks of culturing in regular or osteogenic media. Data are expressed as average±SD. The results were statistically analyzed using unpaired t-tests, n=3. For all the tests, the threshold was set to p<0.01 for "statistically very significant." Statistical significance is indicated by ** (very significant) for indicated samples.
Figure 10:
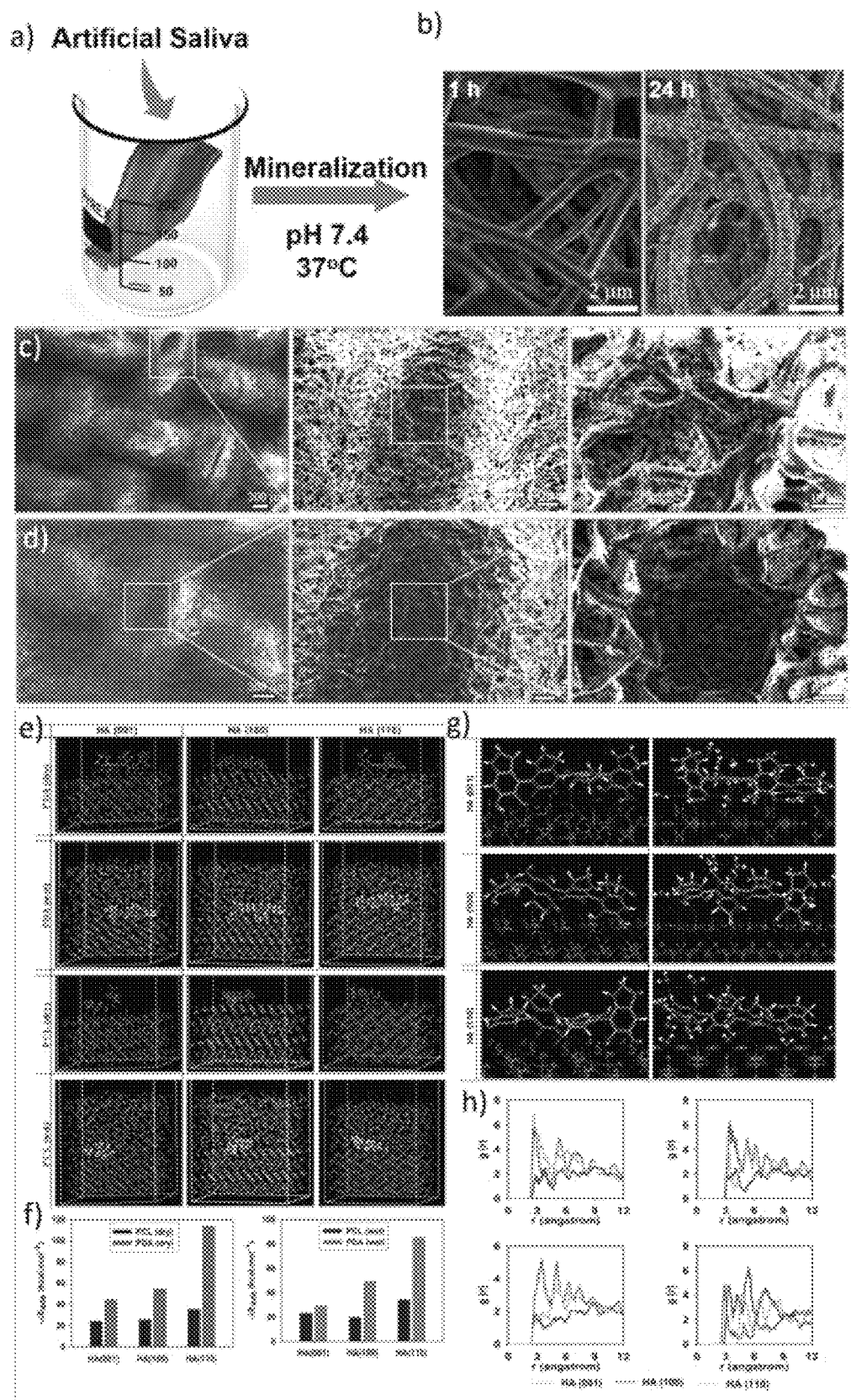
FIG. 10. (a) Incubation of PCL-PDA membranes in artificial saliva resulted in mineralizing of the membrane, as confirmed by morphological evaluation via SEM at different time points (b). (c) Morphological patterning also affects mineralization as investigated for two sets of membranes with 50 μm (c) and 100 μm (d) openings at different magnifications. (e) Side views of final snapshots of PCL and PDA molecules over three hydroxyapatite (HA) surfaces, HA (001), HA (100), and HA (110), in dry and wet environments. The PCL and PDA are shown in Ball & Stick style and solvent and HA surfaces are displayed in Line style. The color code is: carbon gray, oxygen red, hydrogen white, nitrogen blue, calcium green and phosphorus purple. (f) The computed adsorption energies of PDA and PCL molecules with three HA surfaces obtained at the end of MD simulations in dry and wet environments. (g) The hydrogen bonding interactions of PDA molecules with different crystallographic surfaces of HA and water solvent molecules. The H-bonds are shown in dashed blue lines. PDA and water molecules are shown in Stick and Ball & Stick models, respectively. (h) Radial distribution functions (RDFs) of oxygen atoms in PDA with (a) calcium atoms (b) phosphorus atoms, and (c) oxygen atoms in $PO_4$ groups in HA; RDFs of nitrogen atoms in PDA with hydroxyl oxygen atoms in HA.
Figure 11:
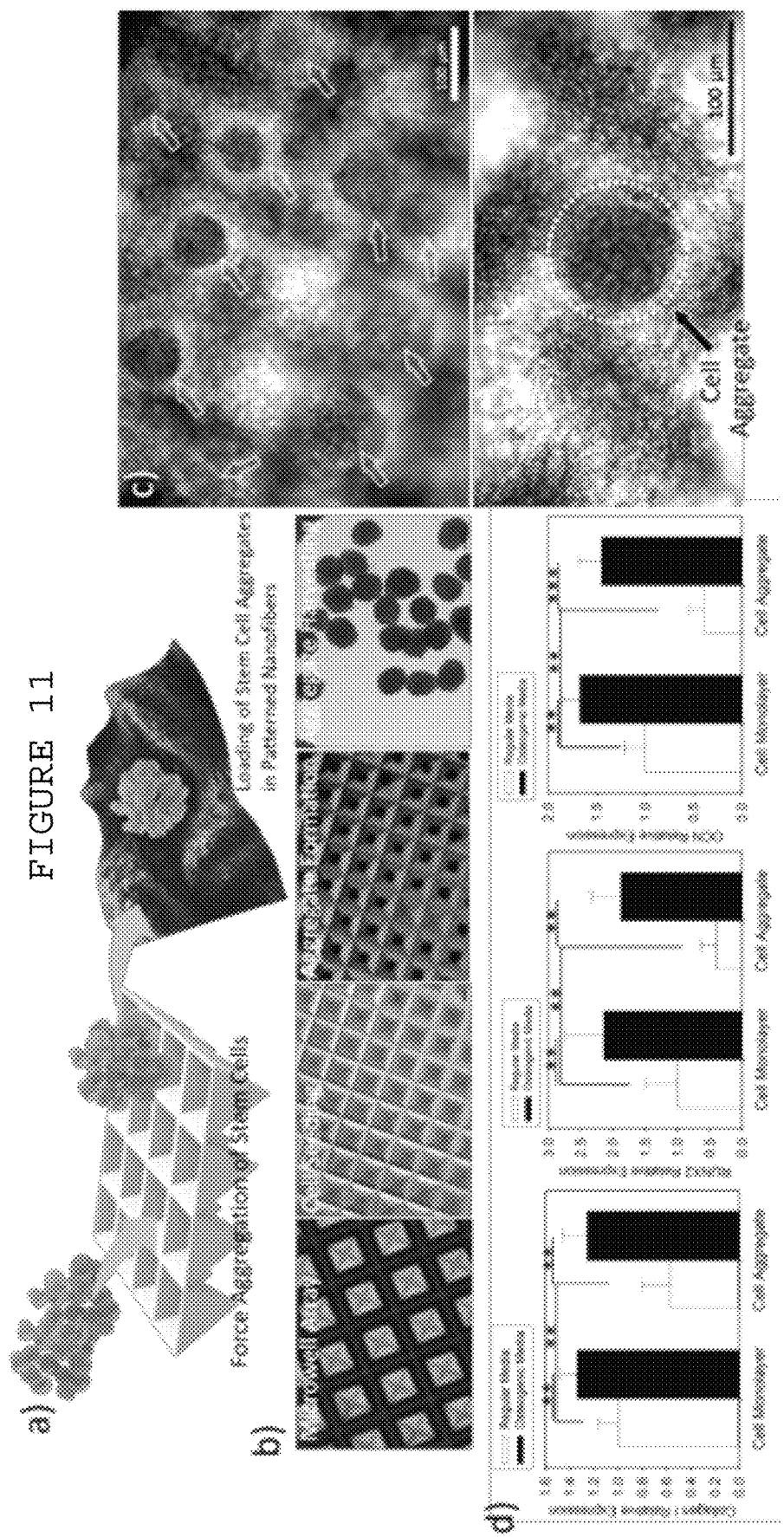
FIG. 11. (a) PDSC aggregates were created via force aggregation and then loaded on micropatterned PCL-PDA membranes. (b) Cell aggregates were formed by seeding cells on pyramidal PDMS micro-wells (Length, width, and depth all 400 μm) followed by gentle centrifugation. After 24 h of culture, formed aggregates (average size: 150 μm) were harvested. Scale bar=200 μm. (c) Bright-field micrographs show localization of stem cell aggregates inside nanofibrous-based micropatterned niches. (d) Real-time PCR analysis of the osteo-differentiation of PDSC monolayer culture compared to 3D cell aggregates cultures on PCL-PDA membranes after four weeks in regular or osteogenic media. Expression of three osteo-genes, Col1, RUNX2, and OCN, were evaluated with reference to the housekeeping gene GAPDH. Data are expressed as average±SD. The results were statistically analyzed using unpaired t-tests, n=3. For all the tests, the threshold was set to p<0.01 for "statistically very significant" and p<0.001 for "statistically extremely significant". Statistical significance is indicated by  (very significant) and * (extremely significant) for indicated samples.
Figure 12:
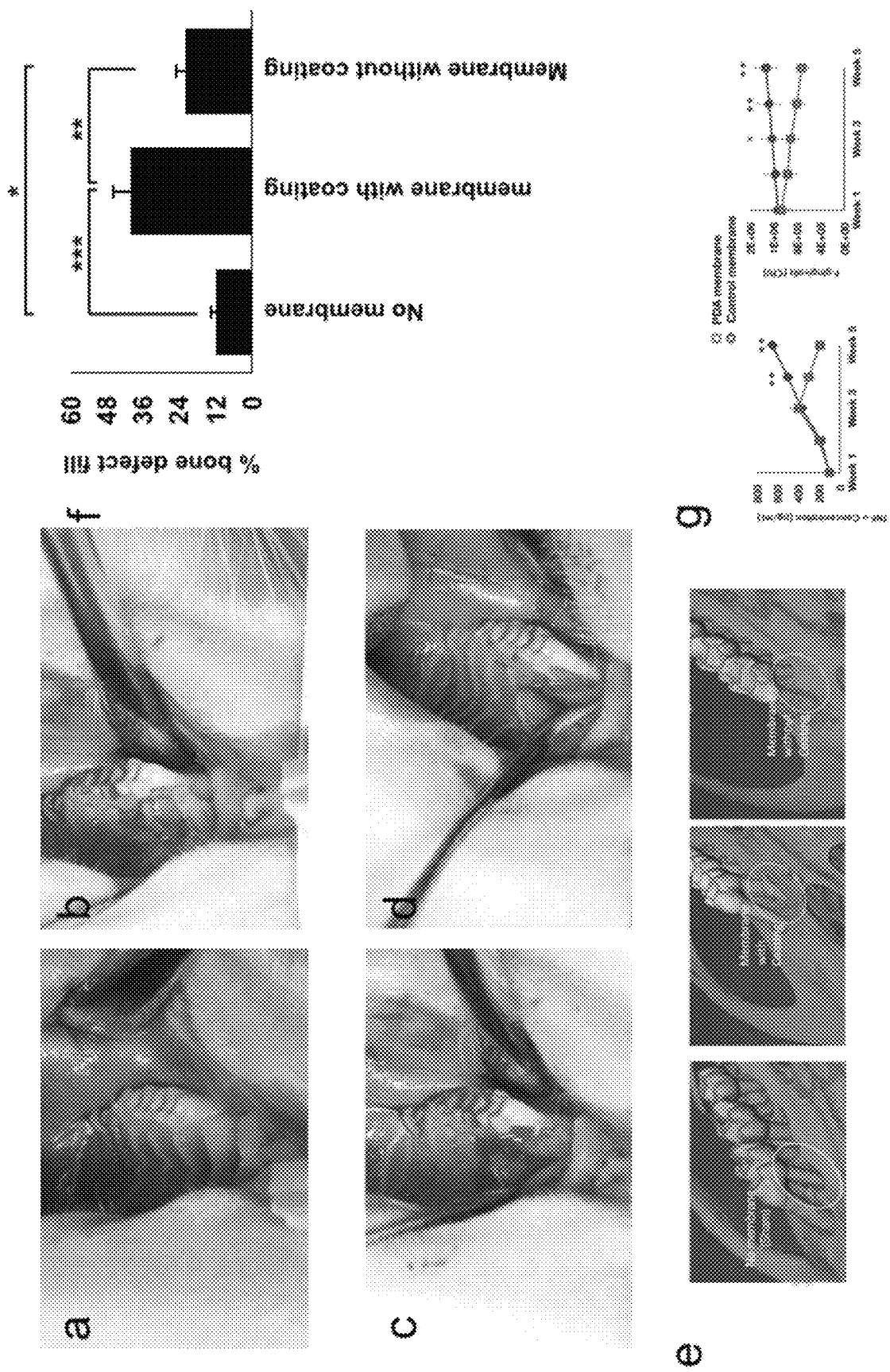
FIG. 12. Rat periodontal defect model. (a-d) Description of rat periodontal defect design: mucoperiosteal flaps were elevated uncovering the alveolar bone adjacent to the lingual aspect of the first maxillary molar. The alveolar bone covering the root surfaces was removed with a dental bur, creating a periodontal window defect, and the periodontal membrane was placed into the defect site. (e) Micro-CT analysis of the rat maxilla showing the defect sites with no treatment, application of the PDA-coated membrane and the control membrane with no coating. All the specimens were standardized and micro-CT images were calibrated for proper comparative analysis. (f) Semi-quantitative analysis of the percentage of bone defect fill. (g) the inflammatory and bacterial profile at the defect site up to five weeks of application of the membrane confirming the antibacterial properties of the membrane in vivo.
Figure 13:
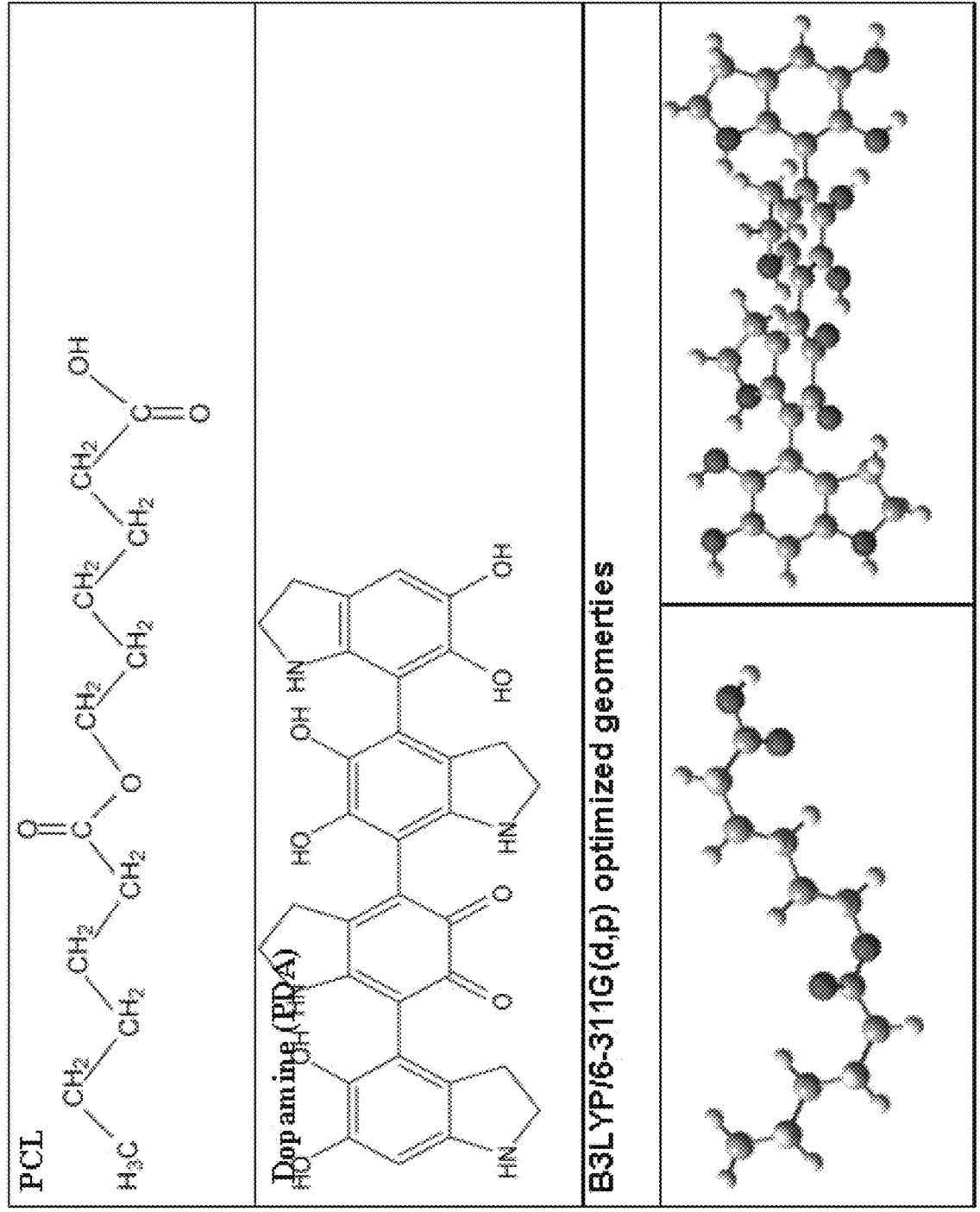
FIG. 13. Chemical structures of poly caprolactone (PCL) and dopamine, and their optimized geometries derived from DFT calculations at the B3LYP/6-311G(d,p) level of theory.
Figure 14:
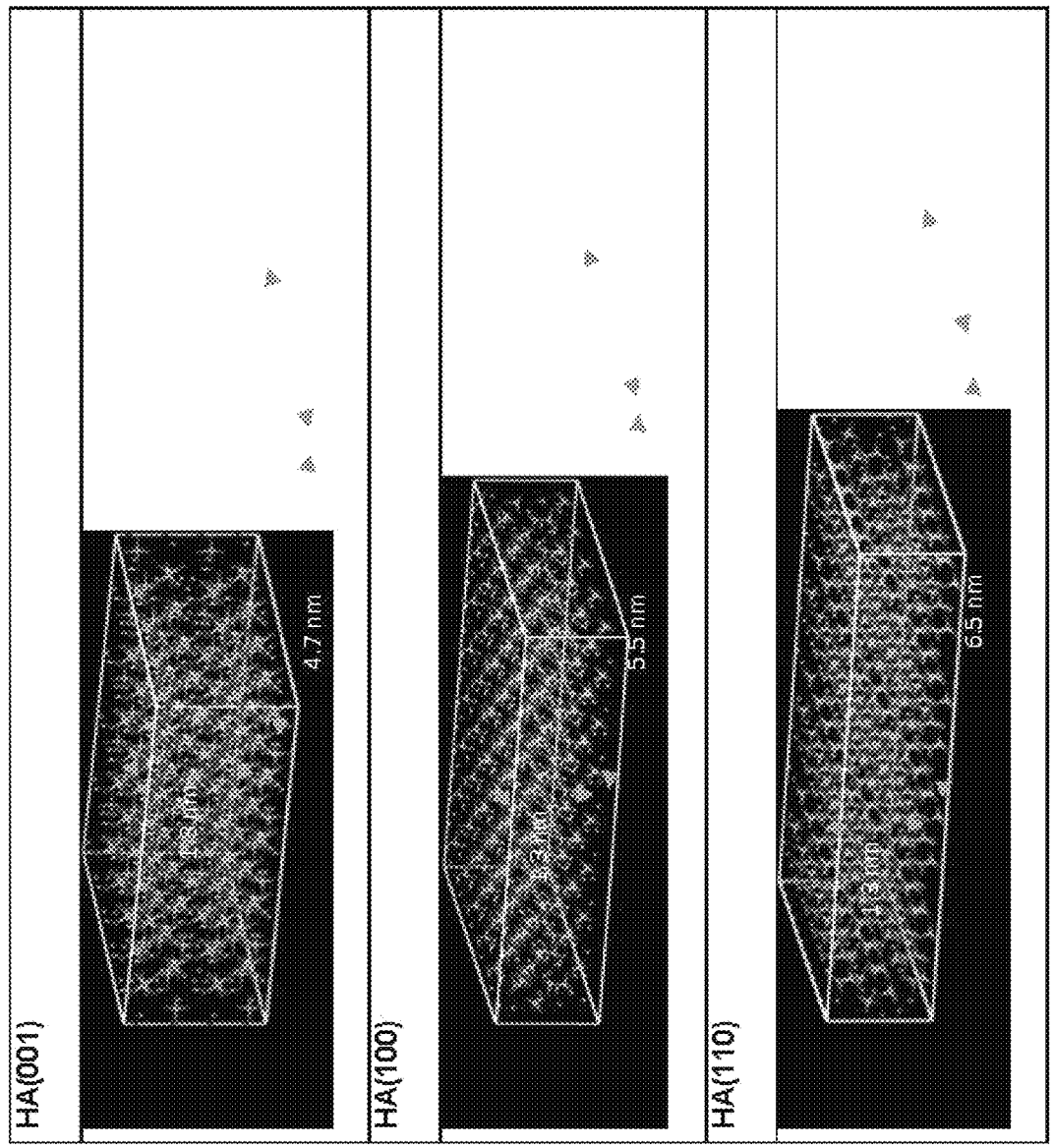
FIG. 14. The three constructed crystallographic hydroxyapatite (HA) surfaces. The color code is: oxygen red, hydrogen white, calcium green, and phosphorus purple.

FIG. 1 illustrates fabrication of an exemplified membrane made of FDA-approved synthetic polymer poly (ε-caprolactone) (PCL) coated with polydopamine Testing demonstrated the PCL-PDA membrane exhibits and enables a surprising and unexpected combination of properties and/or functionalities, including tunable in vitro degradation (FIG. 2), tunable mechanical strength (FIG. 3), binding capacity with several cytokines/growth factors including stromal cell-derived factor 1 (SDF-1α) cytokine, recombinant human bone morphogenetic proteins-2 (rhBMP-2) growth factor, and Vascular endothelial growth factor (VEGF) (FIG. 4), fluorescence (FIG. 5), ability to culture viable periodontal ligament stem cells (FIG. 6) in controlled patterns (FIGS. 7 and 9), micro and nano processability (FIG. 8), mineralization (FIG. 10), and osteodifferentiation (FIG. 11).

In an embodiment, an application for the membranes described herein is as a barrier to exclude epithelium from tooth root surfaces. Multiscale design has been used to mimic the complexity of extracellular environment of periodontal tissue in order to make functional tissue constructs for periodontal regeneration. Suitability of the membrane for treating periodontal disease has been demonstrated on animal (rat) subjects. The membranes implemented in rats have been shown to partially regenerate lost periodontal tissue with new bone, periodontal ligament, and cementum.

Example 2

Figure 20:
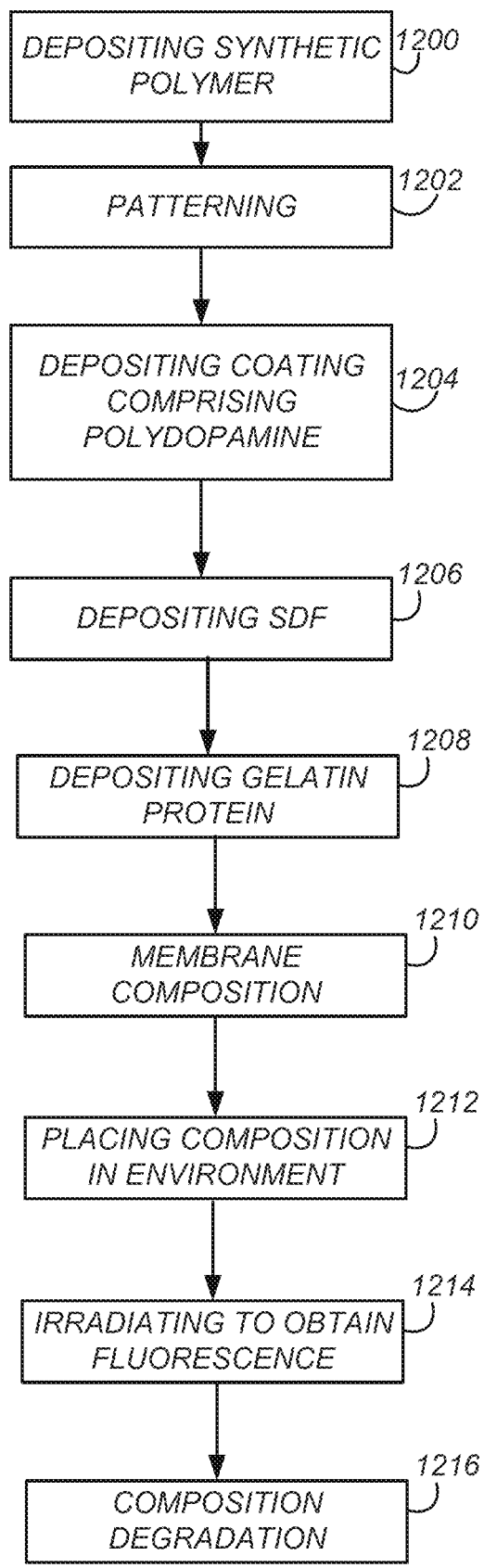
FIG. 20. Flowchart illustrating a method of making a membrane composition in accordance with embodiments of the invention.

Process Steps for Fabricating a Composition in Accordance with Described Embodiments Process Steps FIG. 20 illustrates methods of making membrane compositions in accordance with embodiments described herein, by integrating micro and/or nanotechnology techniques, as well as using the novel membrane compositions for tissue regeneration.

Block 1200 represents depositing a membrane comprising a synthetic polymer. In one or more examples, a structure, matrix, or network of fibers is deposited on a substrate, wherein the fibers each comprise the synthetic polymer and together form a fibrous membrane. In one example, the synthetic polymer is poly(ε-caprolactone). Example deposition techniques include, but are not limited to, electrospinning, sol-gel techniques, and plasma spraying, and any other suitable technique for achieving the desired result.

Block 1202 represents micropatterning niches, wells, openings, or cavities in a surface of the membrane, using a mold or photolithography. In one or more embodiments, the niches have a lateral dimension of less than 250 micrometers (e.g., in a range of 20-250 micrometers). In one or more examples, the niches have a width of 50-700 micrometers and/or a depth of 10-100 micrometers. Example patterning techniques include, but are not limited to, molecular ultraviolet (UV)-based photopatterning, microcontact printing, and morphological micropatterning.

Block 1204 represents depositing a coating comprising polydopamine on the synthetic polymer.

Block 1206 represents depositing several cytokines/growth factors including Stromal cell-derived factor 1 (SDF-1α) cytokine, recombinant human bone morphogenetic proteins-2 (rhBMP-2) growth factor, and Vascular endothelial growth factor (VEGF) on the polydopamine.

Block 1208 represents optionally depositing/coupling/blending a gelatin protein to the membrane, wherein in embodiments, a composition of the gelatin protein can tune degradation and mechanical strength of the membrane and can control release of therapeutic proteins from the membrane. In illustrative embodiments, a ratio of the gelatin protein to the poly(ε-caprolactone) in the membrane is in a range of 1:1 to 1:4 so that the membrane degrades after a time in a range of about 4-6 months; exhibits a Young's modulus in a range of about 1-10 MPa; and exhibits a tensile strength in a range of about 1-4 MPa. In one or more embodiments, the Young's modulus of the membrane is tuned to be close to that of the surrounding tissue.

Block 1210 represents the end result, an embodiment of a membrane composition in accordance with those described herein, including the synthetic polymer, the polydopamine, and the SDF, rhBMP-2, VEGF, and optionally the gelatin protein. In one or more embodiments, each of the fibers in the fibrous membrane comprises the synthetic polymer, the polydopamine, and the SDF, rhBMP-2, VEGF, and optionally the gelatin protein. Example fibers include, but are not limited to, nanofibers each having a diameter in a range of about 100-2500 nanometers. Porosity of the (e.g., fibrous) membrane composition allows conductivity/collection of nutrients needed for bone growth. In one or more examples, pores in the membrane composition (e.g., between the fibers) have a width in a range of about 1 to about 20 micrometers.

Block 1212 represents placing a membrane composition in an in vivo environment where the membrane composition provides guided tissue generation. In embodiments, the membrane composition releases the SDF over time so that the SDF attracts stem cells onto the membrane from the environment (e.g., from blood, gingival tissue, and/or bone). The niches collect or seed the stem cells so as to selectively promote growth of bone tissue and/or periodontal ligament tissue in the environment and on/in/through the membrane composition. In one or more embodiments, the stem cells are gingival mesenchymal stem cells exhibiting more than 60% in vitro differentiation when disposed on the membrane composition.

The polydopamine absorbs calcium and phosphate from the in vivo environment to promote bone growth and/or transform the stem cells into bone and the membrane comprises a barrier that suppresses epithelial tissue growth so as to promote the bone growth over other (e.g., non-bone) tissue growth in the in vivo environment. In one or more embodiments, an extracellular matrix secreted by the stem cells is formed and remodels the membrane composition.

In one or more embodiments, the niches have a pattern selected to facilitate the stem cells' adhesion to the membrane.

Example environments include, but are not limited to, the region between gum tissue and a root surface of a tooth. In the presence of saliva in the environment, the membrane composition accelerates mineral deposition of hydroxyapatite and the polydopamine acts as an adhesive and adheres to the root surface of the tooth. Additionally, however, the membrane composition may be used in accordance with methods described herein for tissue generation more generally in other parts or environments of animal and human subjects. Thus, as an alternative to positioning the described compositions between a gum and a root surface of a tooth, the composition can instead be positioned as appropriate in such other areas in the subject, to achieve the desired tissue generation in those locations. Such alternate applications include, without limitation, diabetic wound healing and bone fractures, among many others.

Membranes in accordance with embodiments described herein thus can also be used in any applications (e.g., orthopedic) where bone regeneration/generation is desirable (e.g., bone graft). In one or more examples, the membrane is placed in a region (e.g., socket), e.g., prior to placement of an implant. The membrane promotes growth of bone graft growth to the implant.

Block 1214 represents irradiating a membrane composition in accordance with embodiments described herein in the in vivo environment with electromagnetic radiation so that the polydopamine emits fluorescence in response to the electromagnetic radiation. The fluorescence intensity changes depending on a pH of the in vivo environment. In one or more examples, the pH that is neutral indicates the in vivo environment is healthy and the pH that is acidic indicates the environment has inflammation. In one or more embodiments, a detector or detection system is positioned to detect and/or analyze the color of the fluorescence and a light source (light emitting diode or laser) is used to irradiate the polydopamine with the electromagnetic radiation.

Block 1216 represents allowing the membrane to degrade after sufficient bone growth has been achieved. In one or more examples, the bioactivity of the membrane is such that the membrane composition degrades after sufficient bone growth (e.g., after about 2-6 months).

Example 3

A series of nanofibrous membranes with tunable mechanical and degradation properties were developed for periodontal tissue regeneration. Dopamine based biomimetic surface coating was utilized to promote the adhesion of cells and therapeutic proteins. To demonstrate potential applications of these membranes for craniofacial bone tissue engineering, we show that these biocompatible membranes are multifunctional and can deliver patient-derived dental stem cell monolayers or cell aggregates. Dopamine polymerization can be altered to add pH-dependent fluorescent properties to the structure, which can be used to monitor local inflammation in a label-free manner. Molecular and morphological micropatterning of the membranes can also be utilized to control cellular localization. The presence of polydopamine can promote osteogenic differentiation of dental-derived stem cells by accelerating hydroxyapatite mineralization. Quantum mechanical and molecular dynamics simulations were performed to demonstrate the interactions between hydroxyapatite crystals and the polydopamine-modified surface. These biomimetic membranes have advantages as cell/protein delivery platforms for craniofacial tissue engineering.

In the current study, we have developed an osteoconductive periodontal membrane with tunable mechanical and degradation characteristics. We have combined multiple physicochemical techniques to expand the properties of this newly developed periodontal membrane. The electrospun membranes were developed using an FDA-approved synthetic polymer, poly (ε-caprolactone) (PCL). Although this biocompatible polymer has been used for various biomedical applications, to make it suitable for cell adhesion, further surface treatment is required. Various chemical and physical surface modifications have been reported before. Due to the unique adhesive properties of polyphenols, polydopamine (PDA) in particular has recently attracted significant interest in many fields as a multifunctional thin film coating. Polydopamine is a synthetic melanin-like polymer that mimics the composition of the protein secreted by mussels for attachment to surfaces in wet conditions with a high binding strength. Dopamine can self-polymerize at a basic pH, which leads to the coating of the immersed surfaces. It has been reported that the presence of dopamine-based structures provides favorable adhesive properties even in wet conditions and can also accelerate the mineral deposition of hydroxyapatite in the presence of simulated body fluids. In addition, it has been reported that this biomimetic polymer can also promote cellular adhesion and affect cell fate. In order to investigate the potential application of the PDA-coated membrane we have developed for craniofacial bone tissue engineering, here we have used several types of dental-derived human mesenchymal stem cells including gingival-derived mesenchymal stem cell (GMSCs) and human periodontal ligament stem cells (PDLSCs) in addition to human bone-marrow mesenchymal stem cell (hBMMSCs) to confirm the in vitro functionality of the membranes.

Multiple molecular, UV-based photopatterning and microcontact printing, and morphological micropatterning approaches have been utilized as engineering tools to control the localization and fate of mesenchymal stem cells. Moreover, the membrane we have developed can be further modified with functional proteins including cytokines, growth factors, and extracellular proteins. These modifications will lead to further manipulation of the chemical features of the substrate in accordance with physical patterns in order to regenerate heterogeneous tissues like the periodontium. Here we have developed membranes with multiscale architecture to enhance periodontal tissue regeneration. Such a multiscale design has the potential to mimic the complex extracellular environment of periodontal tissue and make functional tissue constructs for periodontal regeneration.

Results and Discussion

Figure 15:
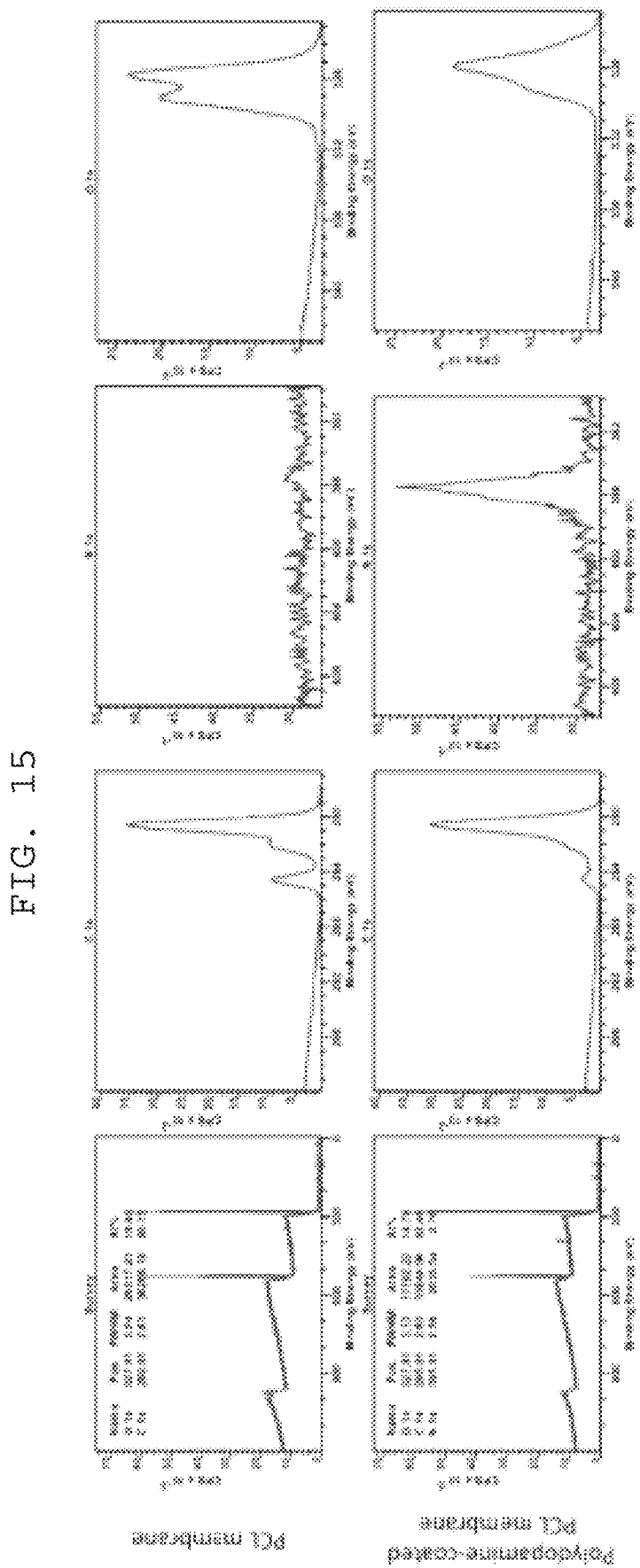
FIG. 15. Survey scan XPS spectra for PCL and PCL-PDA membranes.

Here we have utilized an electrospinning process to fabricate nanofibrous membranes based on poly(ε-caprolactone) (PCL) (FIG. 1a). Solutions of PCL in 1,1,1,3,3, 3Hexafluoro-2-propanol (HFIP) were electrospun under a variety of different conditions, including manipulation of the polymer concentration (5-20%), voltage (5-25 kV), and infusion rate (1.0-5.0 ml/h). The optimized conditions were found to be 10% solution at 15 kV with a tip-to-target distance of 8-10 cm. The infusion rate was a constant 2.5 ml/h for a total of 0.5 ml per membrane. Changes in fiber morphology was achieved by tuning the electrospinning conditions as proposed before. Inspired by mussel adhesive proteins that contain 3,4-dihydroxy-L-phenylalanine (DOPA), the developed membranes were coated in a biomimetic fashion using polydopamine (PDA). Dopamine can spontaneously self-polymerize at a slightly basic pH (>8). As demonstrated in FIG. 1b, this biomimetic approach was utilized to coat the PCL nanofibers and form PDA-coated membranes. Based on scanning electron micrographs (FIG. 1c), the presence of PDA does not change the morphology of fibers. Coated and non-coated PCL nanofibers showed uniform, bead-free, randomly oriented nanofibers with an average diameter of 282±50 nm and interconnected porous structure with pores on the order of 2.1±0.7 μm. The thickness of the coating can be adjusted by either varying the dopamine concentration or the time of polymerization. Here, we have coated a PCL-based surface at a constant dopamine concentration of 2 mg/ml and the time-dependency of the coated thickness is shown in FIG. 1d. As shown, the coating level reaches a plateau after about 16 h of reaction. In addition, XPS analysis confirmed the presence of the monomeric dopamine elements (i.e., carbon, oxygen, and nitrogen), in the respective spectra for the PDA-coated nanofibers (FIGS. 1e, f). In addition to a reduction in the oxygen (O 1s peak) content of PCL, the N1s peak at 295 eV (FIG. 2f and FIG. 15) confirmed successful deposition of a dopamine-containing coating.

Both the PCL and PDA-coated PCL (PDA-PCL) membranes degraded over time in vitro (FIG. 2a). The coated membranes degraded at slightly faster rates than the unmodified membrane. The presence of an oxidative agent, like $H_2O_2$, can facilitate degradation of the PDA coating as well as the core PCL, as reflected in an increase in degradation rate and decrease in half-life (FIG. 2d). To suit a wide range of medical and dental applications, regenerative membranes need to provide wide range of degradation properties. Simple incorporation of gelatin into the PCL solution at various concentrations prior to electrospinning can provide faster degradation in the absence (FIG. 2b) or presence of digestive enzymes like collagenase (FIG. 2c). Using this simple manipulation, degradation of these membranes can be tuned to take about 2-10 weeks (FIG. 2f).

Figure 3:
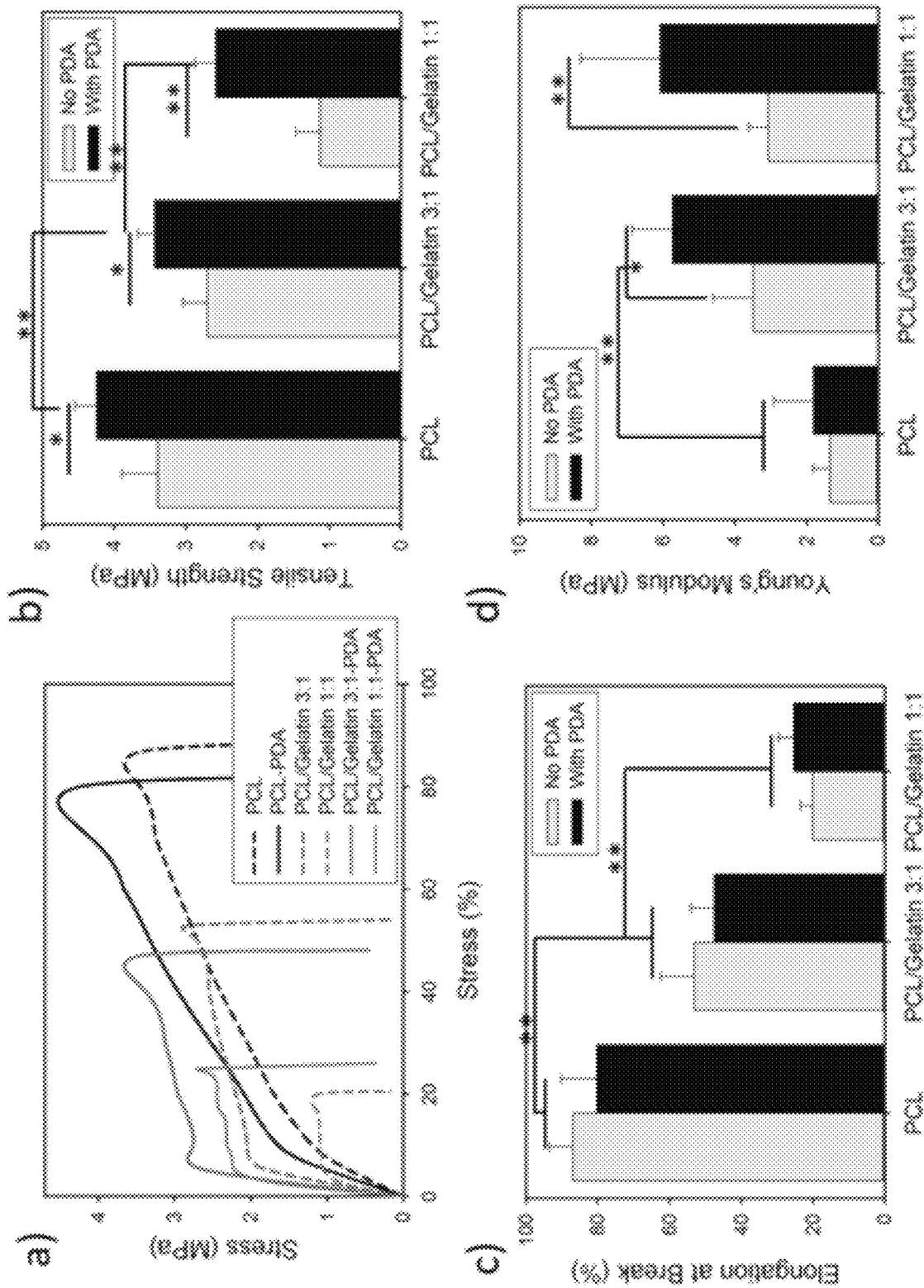
FIG. 3. (a) Mechanical characterization of PCL-PDA-based electrospun membranes as tested by uniaxial tensile experiments. Tensile strength (b), elongation at break (c), and Young's modulus (d) calculated from tensile data. Data are expressed as average±SD. The results were statistically analyzed using unpaired t-tests, n=3. For all the tests, the threshold was set to $p<0.05$ for "statistically significant" and $p<0.01$ for "statistically very significant". Statistical significance is indicated by * (significant) and ** (very significant) for indicated comparisons.

Polydopamine coating as well as the addition of gelatin will also affect the mechanical properties of the final construct. FIG. 3 demonstrates the tensile properties of membranes and their stress-strain curves. The tensile strength and Young's modulus of the nanofibers were slightly enhanced after PDA coating. However, more significant changes (p<0.01) in these properties can be accomplished when gelatin is included in the formulation. Based on our data, it is possible to increase the modulus of the membranes over six-fold (1-6 MPa) to expand the range of biomedical applications of these membranes.

Figure 4:
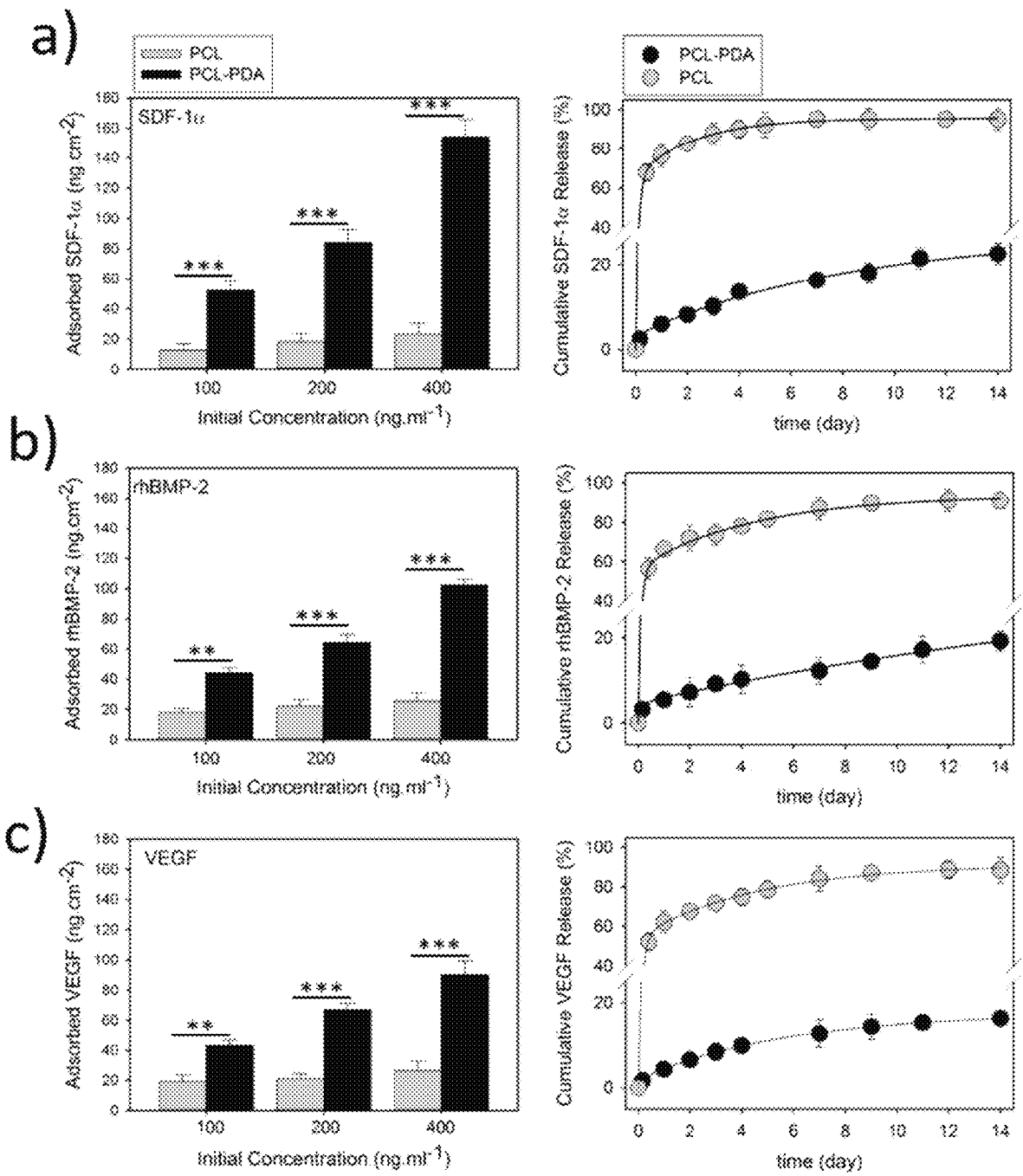
FIG. 4. Binding capacities of PCL and PCL-PDA nanofibrous membranes were evaluated after incubating them with Stromal cell-derived factor 1 (SDF-1α) cytokine (a), recombinant human bone morphogenetic proteins-2 (rhBMP-2) growth factor (b), and Vascular endothelial growth factor (VEGF) (c) at concentrations of 100, 200, or 400 ng/ml for 12 h at 4° C. under continuous, gentle shaking. Cumulative release profiles of these cytokine/growth factors over two weeks at 37° C. are presented at right. Data are expressed as average±SD. The results were statistically analyzed using unpaired t-tests, n=3. For all the tests, extremely significant". Statistical significance is indicated by  (very significant) and * (extremely significant) for indicated comparisons.
Figure 16:
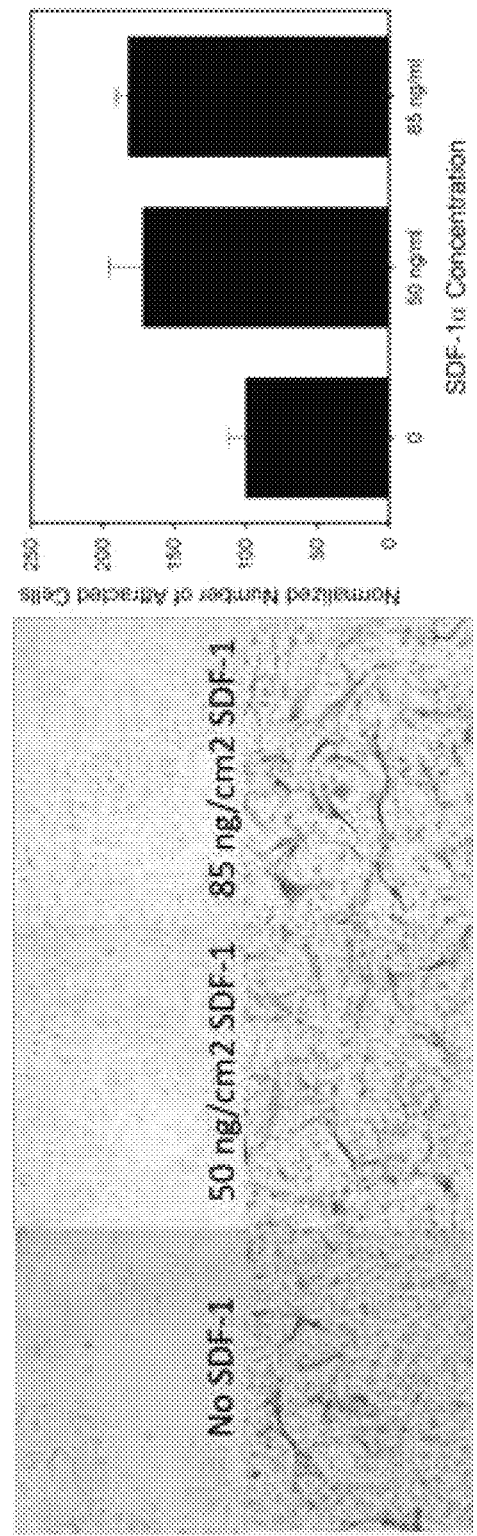
FIG. 16. Migration of PDLMSCs as studied using a modified Boyden chamber assay. Representative images of migrated cells (stained in blue) in the lower site of the Transwell membrane after 20 h. Cell migration assays were performed with 50 and 85 ng/ml loaded PDA-PCL membranes. (Right) Quantification of relative stem cell migration (Chemotactic index) for studied groups.
Figure 18:
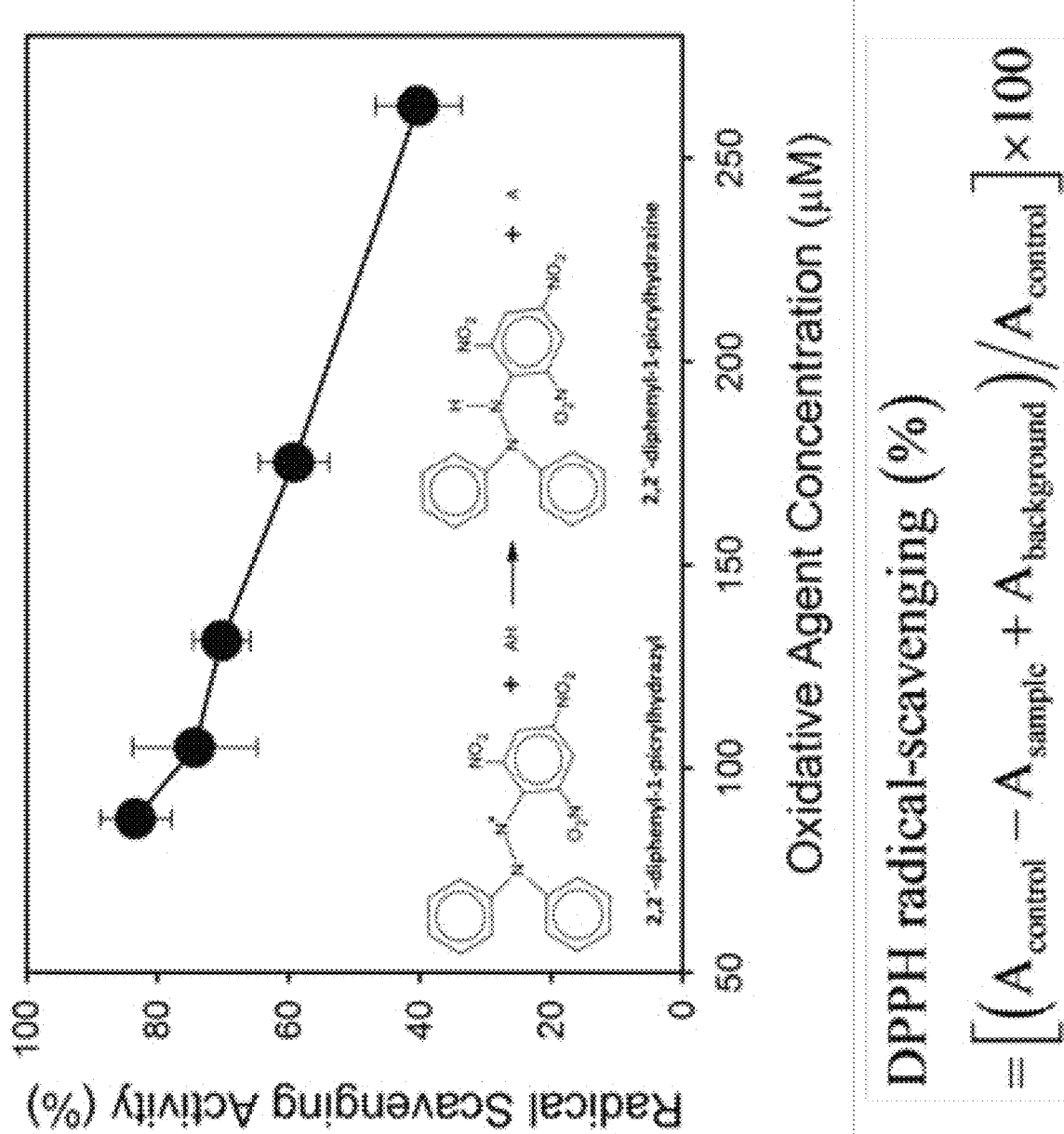
FIG. 18. Radical scavenging activity of PDA-PCL membranes as a function of oxidative agent concentration.

Precise presentation of therapeutic macromolecules is a critical demand in tissue engineering. For example, sustained release of growth factors (GFs) can induce host cell infiltration as well as improve engraftment of delivered cells to facilitate tissue regeneration. Delivery of therapeutic proteins generally requires incorporation of specific carriers to encapsulate, protect, and provide sustained release of proteins. Various types of nano-and microstructures have been reported to control the delivery profiles of GFs. Here we have shown that the unique properties of a PDA layer can provide enough adhesion to adsorb substantial amounts of GFs and provide sustained release of these GFs without any further need for a carrier. Proof-of-concept results for two GFs, namely recombinant human bone morphogenetic proteins-2 (rhBMP-2) and vascular endothelial growth factor (VEGF), and a cytokine, stromal cell-derived factor 1 (SDF- 1α), are shown in FIG. 4. Incubation of these proteins with PDA-coated membranes will provide high binding levels due to the semi-covalent interaction of the primary amine and/or thiol groups of proteins with PDA surfaces. These nonspecific interactions can be used to bind/load various kinds of proteins regardless of their nature. In vitro functional assays for each of these three proteins (FIG. 4) verified that the binding will not compromise the structure or function of these proteins. For instance, Transwell assay experiments verified that sustained release of SDF-1α can enhance recruitment of human bone-marrow mesenchymal stem cells (hBMMSCs) (FIG. 16).

It has been reported that addition of hydrogen peroxide during dopamine self-polymerization can modify the reaction as the oxygen source regulates the intermediate products and makes the final PDA fluorescent. The fluorescence spectra of $PDA_{OX}$-PCL are shown in FIG. 5a. $PDA_{OX}$-PCL can provide a stable fluorescent intensity over a long period of time without photobleaching (FIG. 5b). Interestingly, the resultant fluorescent structure is pH-sensitive: the intensity increases upon reducing the pH, as shown in FIG. 5c. Such intrinsic pH sensitivity can be used to develop label-free biosensors to detect acidic conditions in the oral environment or to monitor inflammation, which can cause a reduction in the local pH in the site of membrane implantation.

In addition, our data confirm that our PDA-modified membrane provides an adherent substrate for cells without affecting their viability. (FIGS. 6a, b). Viability of over 80% has been shown for MSCs seeded on a PDA-PCL membrane after two weeks of culture in regular culture media. Our data show that the rigidity of the substrate (rigid) and the presence of the PDA coating can induce osteogenic differentiation of cultured hBMMSCs, as confirmed by PCR analysis (FIG. 6c). Changes in the expression of early osteogenic markers Collagen type I (Col 1) and Runt-related transcription factor 2 (RUNX2), as well as a late osteogenic marker, osteocalcin (OCN), were evaluated. As shown in FIG. 6c, the presence of a polydopamine layer can actively promote osteogenic differentiation of MSCs. Moreover, changing the cell media from regular to osteogenic accelerated the process.

After four weeks of culturing in regular or osteogenic media, the morphology of MSCs seeded on PCL and PDA-PCL was analyzed using scanning electron microscopy. As shown in FIGS. 6d, e, higher levels of mineralization were clearly observed in the presence of the PDA coating, which is in good correlation with our PCR results. We also examined the effects of preconditioning the membranes with artificial saliva or a therapeutic protein (e.g. rhBMP-2) on the attachment and differentiation of MSCs (FIG. 17). Protein adsorption or hydroxyapatite formation may reduce cellular attachment compared to the intact PDA-coated membrane (FIG. 6f-i). As PDA coating can adsorb ions from the media and initiate mineral deposition, there is not a significant difference in RUNX2 expression levels between specimens pre-incubated in artificial saliva and the intact PDA-PCL. However, the presence of rhBMP-2 can promote osteogenic differentiation of hBMMSCs after four weeks of culture in regular media compared to other groups (FIG. 6i). There was not any statistical difference in the RUNX2 expression level (p>0.5) of cells cultured in osteogenic differentiation media.

Figure 7:
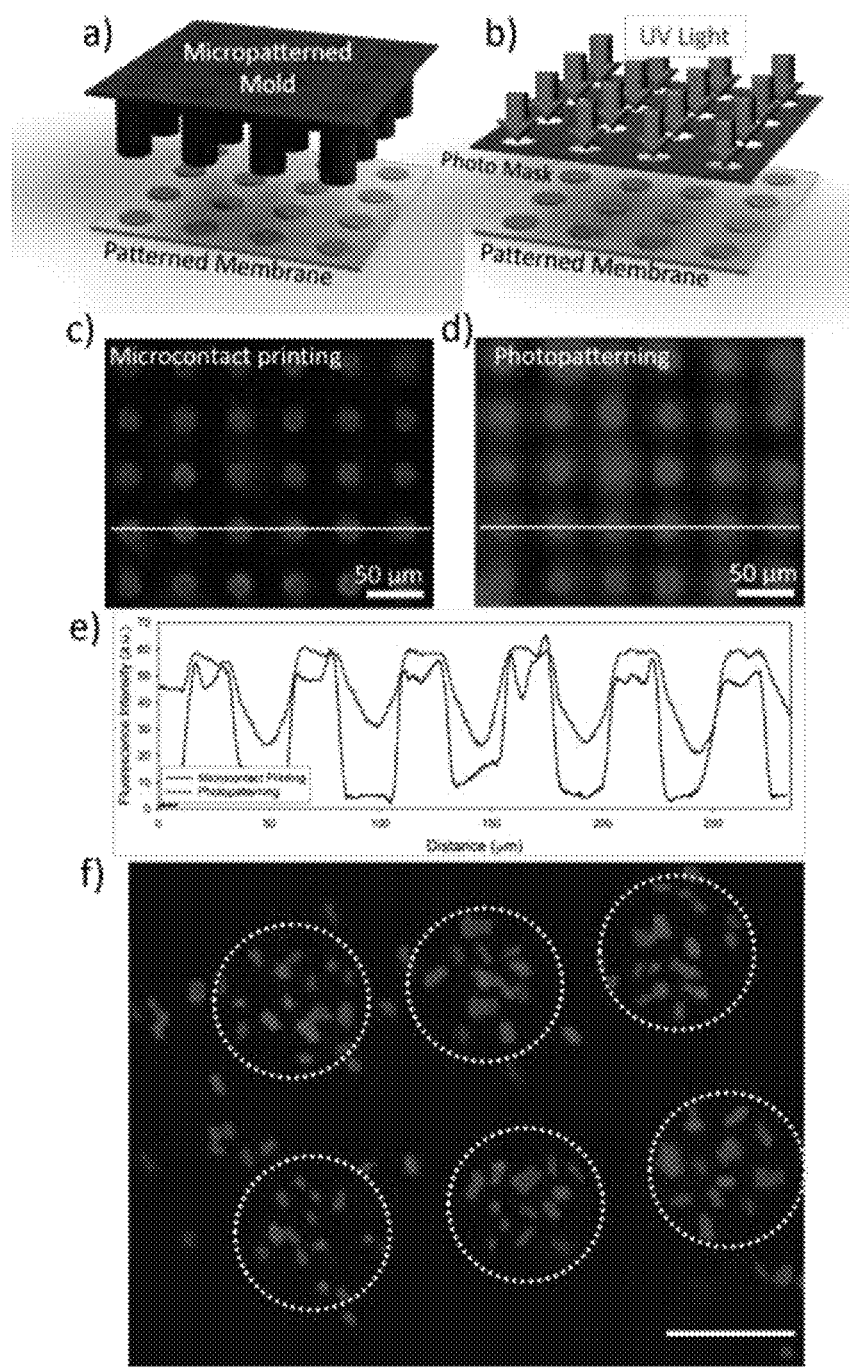
FIG. 7. Schemata of approaches for controlling PDA patterns on PCL membranes in accordance with embodiments described herein via microcontact printing (a) and UV-triggered polymerization (b). Green fluorescence map of adsorbed BSA-FITC on PDA-based patterns as prepared via microcontact printing (c) or photopatterning (d) approaches. (e) Fluorescent intensity change of the adsorbed BSA-FITC along the white lines in (c,d). (f) Fluorescence microscopic images of stem cells after 12 h of culture; cell nuclei stained by DAPI. Estimated spot areas are shown by dotted white circles.
Figure 19:
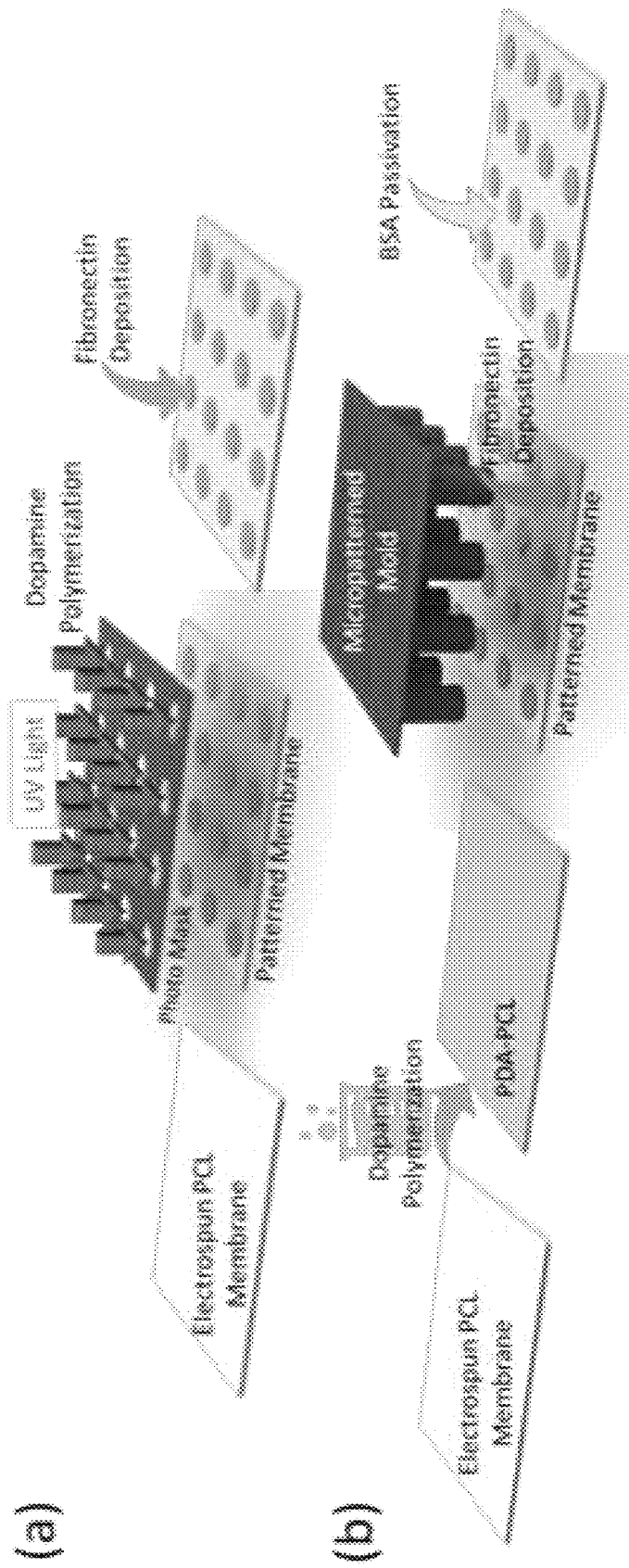
FIG. 19. Schematic representation of the proposed approaches for control PDA patterns on PCL membranes via (a) UV triggered polymerization and (b) microcontact printing.

It has been reported that flat surfaces can be patterned via PDA using different methods including microcontact printing and photopatterning. These two methods are quite widely adopted for making biomolecular spots on the nanometer to micrometer scales. Here we have utilized these techniques for patterning our nanofibrous membranes to localize MSCs, as demonstrated in FIG. 7. For microcontact printing (FIG. 7a), PCL membranes were first coated with PDA as-described before and then a protein-coated stamp was used to make the patterns. The rest of the membrane surface was passivated using polyethylene glycol-thiol (PEG-SH) to prevent nonspecific interactions. The size and shape of patterns can be controlled by changing the stamp design. To make patterns using photopatterning, the PCL membranes were pre-wetted with dopamine molecules and then exposed to UV through a custom-designed photomask (FIG. 7b). UV-mediated polymerization of dopamine has been reported previously. The overnight incubation of the patterned membrane at basic pH after washing and removal of uncoated PDA/dopamine molecules resulted in adsorption of the desired proteins. Deposition of fluorescently labeled bovine serum albumin (FITC-BSA) was used to visualize the quality of patterning as demonstrated in FIG. 19. As shown in FIG. 7 (c-e), microcontact printing achieved greater precision and uniformity than photopatterning, forming a well-defined pattern. That could be due to the lateral diffusion of activated dopamine or polydopamine molecules and possible adsorption of these protein-reactive species at non-target sites. Fibronectin-based coating of patterned membranes was also used to enhance cellular attachment, as shown in FIG. 7f.

Figure 8:
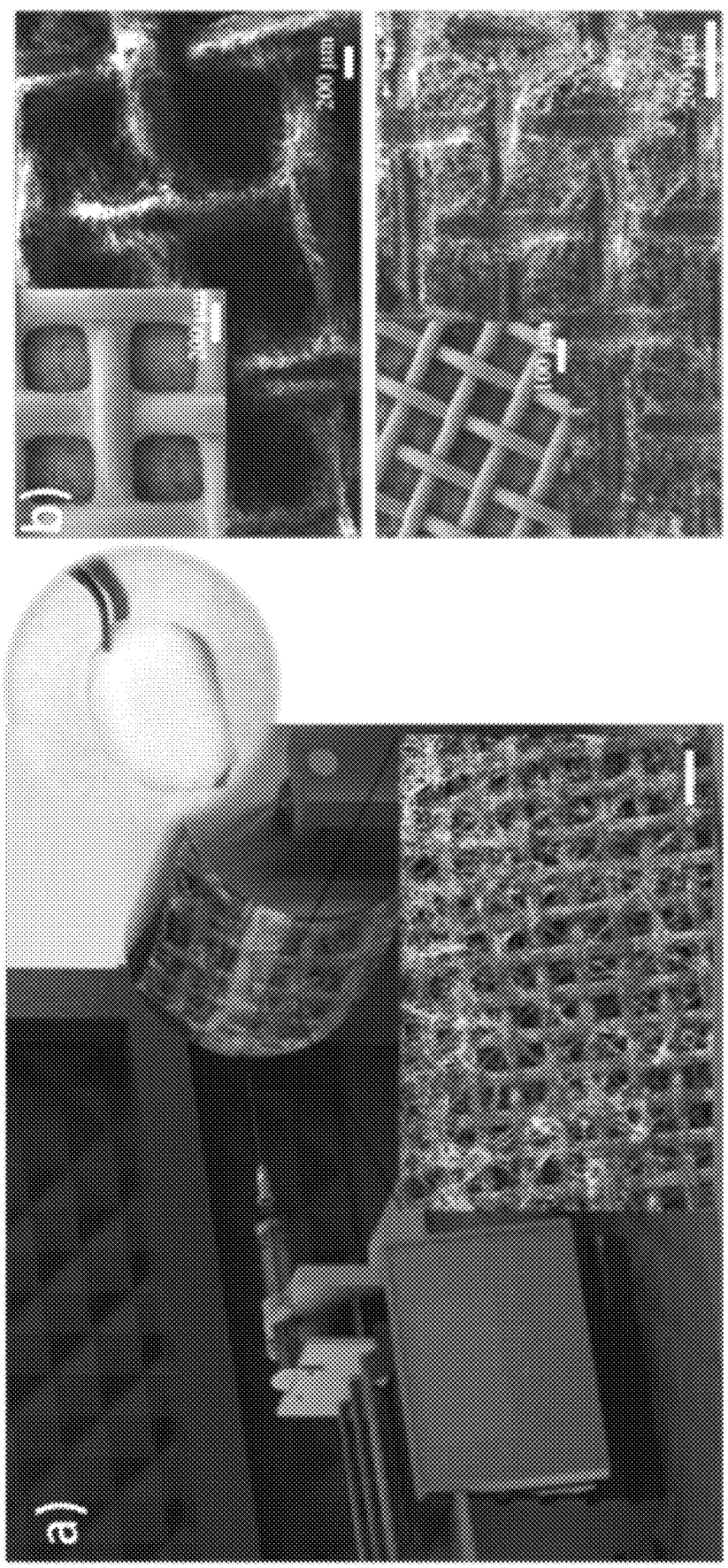
FIG. 8. Morphological patterning of a nanofibrous membrane in accordance with embodiments described herein achieved by using metal mesh as fiber collectors (a). Changing the filament diameter or mesh opening can control the final microstructure, as shown for two meshes (b).

Nanofibrous membranes can also undergo morphological patterning. Here we have used metal substrates with various mesh sizes to generate membranes with various morphologies (FIG. 8). Template meshes with opening sizes of 20-800 μm were used. Due to the nature of electrospinning, fibers typically will not follow the patterns of meshes smaller than 150 μm. Patterned fibers also had a higher elastic modulus due to the alignment of the nanofibers (data not shown).

Next, PDA-coated, morphologically patterned PCL (PDA-MP-PCL) membranes were used as cell substrates. As shown in FIG. 9a, cells followed the patterns, and as the PCL core is biodegradable, cells can manipulate their microenvironments as desired. Scanning electron microscopy images (FIG. 9b) confirmed that cells could actively affect the membrane structure and remodel the membrane even after two weeks of culture in regular media.

The presence of PDA can accelerate adsorption of calcium and phosphate ions from the media and initiate formation of nanoscale particles of hydroxyapatite (FIG. 10a). This intrinsic effect of PDA has been reported before and can be considered a very promising property for bone/dental tissue engineering. After just 24 h of incubation of PDA-modified membranes in artificial saliva or simulated body fluids, formation of hydroxyapatite nanoparticles was detected (FIG. 10b).

Molecular dynamic (MD) simulations were done to examine and compare the adhesion propensities of PCL and PDA molecules over the HA substrates. These classical simulations were conducted under dry (i.e., gas phase or in vacuum) and wet (i.e., aqueous phase or in solution) conditions. For MD simulations in dry environments, the geometry-optimized PCL and PDA derived from QM calculations were placed over all of the HA surfaces. Before molecular dynamics (MD) simulation study of PCL and PDA adhesion over HA surfaces, electronic-scale ab initio quantum mechanics (QM) techniques were applied to optimize the geometries of PCL, PDA and HA. FIG. 10e-h presents the final snapshots of single PCL and PDA molecules resulting from the last steps of MD simulations in both dry and wet environments. From the visualized snapshots it can be noted that PCL and PDA molecules were adsorbed onto all three crystalline HA (001), HA (100) and HA (110) surfaces. The molecular skeletons of adsorbed PCL and PDA substances aligned roughly parallel to the surface. This arrangement maximizes the surface coverage of the adsorbate molecules, which in turn intensifies the adhesion of PCL and PDA molecules. Furthermore, from a closer examination of PCL and PDA bound to all HA surfaces in the absence of water solvent molecules, it can be observed that the oxygen heteroatoms in both adsorbing compounds were oriented towards the surface, likely because of their interfacial electrostatic interactions with surface calcium cations.

To obtain a quantitative perspective concerning the adhesion characteristics of PCL and PDA, the extent of their adhesion was quantified by computing the adsorption energy term ($\Delta E_{ads}$) defined as follows: $\Delta E_{ads} = E_{adsorbate/surface} - (E_{adsorbate} + E_{surface})$. In this equation, $E_{adsorbate/surface}$ represents the potential energy of the entire system (i.e., PCL or PDA adsorbed to HA surface), and the $E_{adsorbate}$ and the $E_{surface}$ respectively indicate the energy of the isolated PCL and PDA adsorbates and isolated HA surfaces. The computed $\Delta E_{ads}$ values for adhesion of PCL and PDA onto each HA substrate in the absence (i.e., dry) and presence (i.e., wet) of solvent molecules are demonstrated in FIG. 10f. All the obtained adsorption energies are negative, quantitatively clarifying the PCL and PDA adhesion to HA surfaces. The PCL and PDA adsorption energies approximately followed the decreasing sequence of HA (110)>HA (100)>HA (001), which signifies the strongest binding of PCL and PDA molecules to plane (110) in crystalline HA materials. Additionally, under both dry and wet situations, the adsorption energy of PDA over each HA surface was higher than that of PCL, implying stronger adhesion of PDA compared to PCL. Upon comparing the $\Delta E_{ads}$ in dry and wet environments, it was found that PCL and PDA adhesion weakened in the presence of water molecules, but the rate of reduction for PCL was significantly lower than that of PDA, probably because of its hydrophobic nature.

To gain detailed insights into the mechanism of PDA adhesion and the interfacial interactions responsible for its binding to HA substrates, the PDA/HA interface was further investigated. FIG. 10g depicts the adsorbed PDA geometry above all three HA surfaces in the absence and presence of water molecules. Observing a single PDA molecule adhered to an HA surface in a dry situation showed that the active functionalities in PDA, including hydroxyl (—OH) and amine (—NH), were involved in interfacial hydrogen bonding interactions with surface hydroxyl and $PO_4$ groups by donating their H atoms. It is worthy of notice that the PDA molecule established a smaller number of H-bonds with the HA (110) surface than with the other surfaces. As a consequence, the strongest PDA adhesion to this surface is ascribed to the existence of more $Ca^{2+}$ cations in the outermost layers of HA (110), which gives rise to strengthened electrostatic interactions with negatively charged sites on PDA (i.e., O and N atoms). In the presence of solvent molecules, PDA substance contributed to fewer H-bonds with surface moieties, and instead formed H-bonds with water molecules, owing to its hydrophilic character. This computational observation is consistent with the observed reduction in adsorption energy under wet conditions. In the case of PCL, almost no interfacial H-bonding was observed in either dry or wet conditions.

To obtain further atomic-scale insights into PDA's interactions with HA surfaces, the radial distribution function (RDF), also called the pair correlation function (g (r)), was assessed. The RDF analyses were done for PDA oxygen and nitrogen heteroatoms with $Ca^{2+}$ cations, and hydroxyl as well as $PO_4$ sites on HA surfaces, and the results are provided in FIG. 10h. RDFs of PDA oxygen atoms towards the calcium atoms displayed an intensified first peak especially over HA (001) and (110) surfaces, which again evidences the electrostatic interactions of O centers in PDA with surface $Ca^{2+}$ sites in HA. The RDFs of PDA oxygen atoms relative to both oxygen and phosphorus atoms of $PO_4$ groups in HA showed similar heightened peaks, revealing that the $PO_4$ fragments in HA could emerge as active sites for PDA adhesion. Moreover, analysis of RDFs between PDA nitrogen heteroatoms and surface hydroxyl oxygen atoms demonstrated multiple high peaks particularly over HA (100) and (110) surfaces, highlighting the PDA surface binding through its interactions with —OH groups positioned in uppermost layers of crystalline HA materials.

As mentioned earlier, such a membrane can be used to deliver various types of cells (e.g. stem cells) and growth factors to contribute toward tissue regeneration at a defect site. Here, by combining morphological patterning and cell aggregates, we proposed a new delivery system (FIG. 11a). To demonstrate this, we made PDLSC aggregates using a force aggregation process as shown in FIG. 11b. Each cell aggregate (diameter 150±5 μm) contained 800-1200 cells. These aggregates were next dispersed on the surface of morphological patterned PDA-PCL (FIG. 11c) and then cultured for two weeks either in regular or osteogenic media. Upregulation of osteogenic markers was confirmed using PCR (FIG. 11d). As the presence of PDA can enhance the mineralization even in regular media, cells cultured on these membranes undergo osteogenic differentiation. However, cells cultured as cell aggregates can also differentiate very efficiently in osteogenic media. Considering that membranes can deliver approximately $40 \times 10^5$ cell/mm$^2$ in the case of cell aggregates compared to $20 \times 10^3$ cell/cm$^2$ for cell monolayers, the therapeutic potential of aggregates would seem to be more promising.

In Vivo Assessment of the Membrane Function: A rat periodontal defect model was utilized. Six, 2 months-old virgin male and female Sprague Dawley rats (Harlan Laboratories, Livermore, Calif.) were utilized for testing the PDA-coated membrane in vivo. Briefly, mucoperiosteal flaps were elevated uncovering the alveolar bone adjacent to the lingual aspect of the first maxillary molars. The alveolar bone covering the root surfaces on the lingual side was removed with a dental bur under saline irrigation. A periodontal window defect of ~1.5 mm in width, 3 mm in length, and 2 mm in depth was created. Subsequently, one of the following membranes was implanted into the defect site: (1) Sham, (2) control collagen membrane (commercially available), or (3) PDA coated membrane. Animals were sacrificed after 6 weeks and micro-CT analysis was used to examine the amounts of bone regeneration. The vertical bone loss around the defect site was evaluated by measuring the distance between CEJ and alveolar bone crest at three different points (mesiolingual (ML), mid lingual (L), and distolingual (DL)) on the lingual of the first maxillary molars.

Conclusions

Here we have described a technological foundation that can be used to expand the capabilities of nanofibrous membranes by modulating various characteristics via incorporation of a biomimetic coating. We have shown the fiber formulations can be tuned to provide a broad range of mechanical and degradation properties. Polydopamine coating can tune the surface representation of the membranes to prolong immobilization and release of target therapeutic proteins. Here we have utilized such membranes in a periodontal setting for craniofacial bone tissue engineering. The ability of structures like the ones used in our membranes to direct the fate of patient-derived dental stem cell monolayers or cell aggregates toward osteogenic differentiation has been described.

Materials and Methods

Chemicals and Biologicals. Unless noted otherwise, all chemicals were purchased from Sigma-Aldrich, Inc. (St. Louis, Mo.). All glassware was cleaned overnight using concentrated sulfuric acid and then thoroughly rinsed with Milli-Q water. All cell culture reagents, solutions, and dishes were obtained from Thermo Fisher Scientific (Waltham, Mass.) except as indicated otherwise.

Stem cell isolation and culture. MSC culture: Young healthy male individuals undergoing third molar extractions were chosen for extraction of gingival and PDL tissues with Institutional Review Board (IRB) approval. GMSCs and PDLSCs were isolated and cultured in regular MSC culture media. Human bone marrow (hBM) MSCs, purchased from Lonza (Lonza Inc. Walkersville, Md.), were used as the control group in this study. To ensure that MSCs were positive for MSC surface markers STRO-1 and CD146 (BD Biosciences, San Jose, Calif.), flow cytometric examination was used. Passage four cells were utilized in all experiments.

Electrospinning. Medical grade ester terminated poly(-caprolactone) in granule form was obtained (Lactel Absorbable Polymers, Birmingham, Ala.); medium molecular weight (Mw=80 kDa). PCL polymer was then dissolved 10% w/w in 1,1,1,3,3,3-hexafluoro-2-propanol (Sigma-Aldrich, St. Louis, Mo.). The PCL solution was electrospun using a 20 kV voltage source and a constant infusion rate of 2.5 ml/h for a total of 0.5 ml per scaffold. Stainless steel metal meshes with different mesh sizes were used as the substrates for making the membranes with morphological patterning.

Polydopamine Coating.

Dopamine hydrochloride was dissolved in 10 mM Tris-HCl (pH 8.5) at concentration of 2 mg/ml, and membranes were immersed into the solution. pH-induced self-polymerization of dopamine changes the color of the solution to dark brown. Membranes were incubated for different lengths of time in the reaction medium at room temperature. The coated membranes were washed with milli-Q water at least three times and dried with nitrogen gas.

To prepare fluorescent membranes, we followed a modified procedure based on previous reports. Briefly, PDA-PCL membranes were suspended in 10 mM Tris-HCl (pH 10) with a dopamine concentration of 2.5 mg/ml. After 1 h of reaction under gentle agitation, 25 v/v% $H_2O_2$ was added to the reaction mixture and allowed to react for another 13 h. Obtained membranes were washed with milli-Q water three times and dried with nitrogen gas before storage or further treatment.

For passivation of polydopamine surface after molecular patterning, membranes were incubated with 2.5 mg/ml thiolated methoxy-poly(ethylene glycol.) (5 kDa) or bovine serum albumin in 10 mM Tris-HCl (pH 8.5) under the nitrogen environment to prevent thiol oxidation.

The 1× simulated body fluid (SBF) was prepared by dissolving appropriate quantities of NaCl, $NaHCO_3$, KCl, $K_2HPO_4$, $MgCl_2$, $CaCl_2$, HCl (1 M), $Na_2SO_4$, and $NH_2C(CH_2OH)_3$ in milli-Q water according to published protocols at 37° C. and the pH was adjusted to 7.4 w. Membranes were incubated in SBF medium for different lengths of time and then washed using milli-Q water and dried using nitrogen gas.

To form cell aggregates, stem cells were trypsinized and aggregates were formed by forced aggregation in AggreWell 400 inserts (Stem Cell Technologies, Vancouver, Calif.) as reported before. Briefly, $1.2 \times 10^6$ cells in 500 µl of single cell suspension ($2 \times 10^6$ cells/ml) were inoculated into micropatterned wells and gently (200×g) centrifuged for 5 min before incubating them for 24 h. Cell aggregates were removed from the wells using a pipette and transferred to patterned membranes.

Characterization.

To assess their in vitro degradation, electrospun samples of PCL and PDA-PCL with an initial weight of 10 mg were immersed in 300 µl phosphate buffered saline at pH 7.4 and incubated at 37° C. for different lengths of time up to 50 days. To measure degradation, samples were removed, rinsed twice in deionized water, dried overnight, and weighed. Three samples per group were used per time point.

The morphology of nanofibers and cultured cells were analyzed using scanning electron microscopy (SEM) (Zeiss Supra 40VP) after coating of membranes with an Iridium layer using South Bay Technology Ion Beam Sputtering (San Clemente, Calif.).

An AXIS Ultra DLD X-ray photoelectron spectrometer (XPS; Kratos Analytical Inc., Chestnut Ridge, N.Y.) was used for elemental surface analysis. This spectrometer uses a monochromatic Al Kα X-ray source with a 200 µm circular pot size and ultrahigh vacuum ($10^{-9}$ Torr). Spectra were acquired at a pass energy of 160 eV for survey spectra and 20 eV for high-resolution spectra of C 1s, O 1s, and N 1s regions using a 300 ms dwell time. For both scan types, 15 kV was applied with an emission of 10 mA. Three scans were performed for survey spectra and 10 scans for each of the high-resolution spectra.

The thickness of the polydopamine coating was evaluated using a Dimension Icon scanning probe microscope (Bruker, Billerica, Mass.). The amount of polydopamine coating was quantified using a modified micro-bicinchoninic acid (BCA) assay. Polydopamine-coated membranes (50 $mm^2$) were treated with 250 µL micro-BCA working solution and the absorbance was measured at 562 nm after for 1.5 h of incubation at 50° C.

For loading of membranes with different therapeutic proteins, SDF-1 α, rhBMP-2, and VEGF were incubated with membranes overnight at 37° C. Unabsorbed proteins in the supernatant were measured with an ELISA kit according to the manufacture's protocol, and sample absorbance was measured using a microplate reader (Bio-Tek Synergy HT, Winooski, Vt.) at a wavelength of 450 nm. The amount of bound protein on the membranes was calculated as the difference between initial amount and the amount found in the supernatant solution. The release kinetics of the proteins were measured using ELISA at different time points in PBS at 37° C.

The fluorescence intensity of chopped membranes was determined using a Photon Technology International quantamaster spectrofluorometer (Horiba, New Jersey, N.J.) at different pH values.

To evaluate the viability of the encapsulated MSCs, a live-dead assay (Calcein AM/ethidium bromide homodimer-1) was utilized after 3,7, and 14 days after culturing in regular culture media according to published protocols. NIH ImageJ software (NIH, Bethesda, Md.) was used to quantify the percentage of live cells.

To identify the morphology of cultured stem cells in different conditions, fluorescence staining was performed using FITC-Phalloidin and DAPI (Vector Laboratories, Burlingame, Calif.).

Quantitative real-time PCR assays were used to analyze gene expression. Cultured cells were recovered from membranes after the course of treatment and total RNA was isolated using Trizol reagent (Invitrogen). RNA was reverse-transcribed and single-stranded cDNA was synthesized using a Superscript III cDNA synthesis kit (Invitrogen). Relative gene expression was calculated using the $2^{-\Delta\Delta Ct}$ method, with normalization to the Ct of the housekeeping gene GAPDH (glyceraldehyde 3-phosphate dehydrogenase). Table 1 describes the primer sequences used on this study.

rials Studio software (version 7). The generalized-gradient approximation (GGA) with Perdew-Burke-Ernzerhof (PBE) scheme was utilized to compute the exchange-correlation interactions with the use of a double numeric polarization (DNP) basis set.

Building HA surfaces. In order to build HA surfaces, a unit cell with chemical formula of $(Ca_{10}(PO_4)_6(OH)_2)$, space group of hexagonal $P6_3/m$, and cell parameters of a=b=9.424 Å, c=6.879 Å and $\alpha'=6=90°$, $\gamma=120°$ were cleaved along crystallographic facets of (001), (100) and (110). These HA surfaces were considered for MD simulation to cover potential interfacial interactions of PCL and PDA with HA substrates. These crystalline HA planes are the most commonly investigated HA surfaces in experiments and were applied in our previous study. Upon cleaving, the

TABLE 1

Oligonucleotide Primers used in RT-PCR Analysis

| Gene | Sequence | Product (bp) |
|---|---|---|
| Runt-related transcription factor 2 (Runx2) | Sense: 5'-CAGTTCCCAAGCATTTCATCC3' (SEQ ID NO: 1); Antisense: 5'-TCAATATGGTCGCCAAA CAG-3' (SEQ ID NO: 2) | 289 |
| Osteocalcin (OCN) | Sense: 5'-CGTGGTGACAAGGGTGAGAC3' (SEQ ID NO: 3); Antisense: 5'-TAGGTGATGTTCTGGGAGGC-3' (SEQ ID NO: 4) | 292 |
| Collagen I | Sense: 5'-GGTGCCCCCGGTCTTCAG-3' (SEQ ID NO: 5) Anti-sense: 5'-AGGGCCAGGGGGTCCAGCATTTC-3 (SEQ ID NO: 6) | 529 |
| Glyceraldehyde 3-phosphate dehydrogenase (GADPH) | Sense: 5'-AGCCGCATCTTCTTTTGCGTC-3' (SEQ ID NO: 7): Antisense: 5'-TCATATTTGGCAGGTTTTT CT-3' (SEQ ID NO: 8) | 418 |

Statistical analysis. Quantitative data were expressed as mean and standard deviation (SD). One-way and two-way analyses of variance, followed by Tukey's test at a significance level of $\alpha=0.05$, were used for comparison among multiple sample means. If necessary, the data were analyzed using Student's t-tests.

Ab initio Quantum Mechanics. Before the molecular dynamics (MD) simulation study of PCL and PDA adhesion over HA surfaces, electronic-scale ab initio quantum mechanics (QM) techniques were applied to optimize the geometries of PCL, PDA and HA. The molecular structures of PCL and PDA are shown in FIG. 1. For PCL molecules, a chain with length of two (i.e., a dimer) was taken into consideration. In case of PDA, as its structure is not well understood, different molecular structures have been suggested in prior computational efforts. The PDA geometry chosen herein is based on a recent work reported by Chai et al. The constructed PCL and PDA geometries were initially optimized using Hartree-Fock (HF)/6-31G(d,p) theory. The geometries so obtained were further relaxed utilizing density functional theory (DFT) approaches and B3LYP hybrid function first with the same 6-31G(d,p) basis set and then with a larger basis function of 6-311G(d,p). The resulting minimum-energy PCL and PDA molecules were subsequently used in atomic MD simulations and their partial charges were determined by using the electrostatic potential (ESP)-based method of ChelpG. All these ab initio QM computations were executed by the Gaussian 09 suite of programs.

Figure 2:
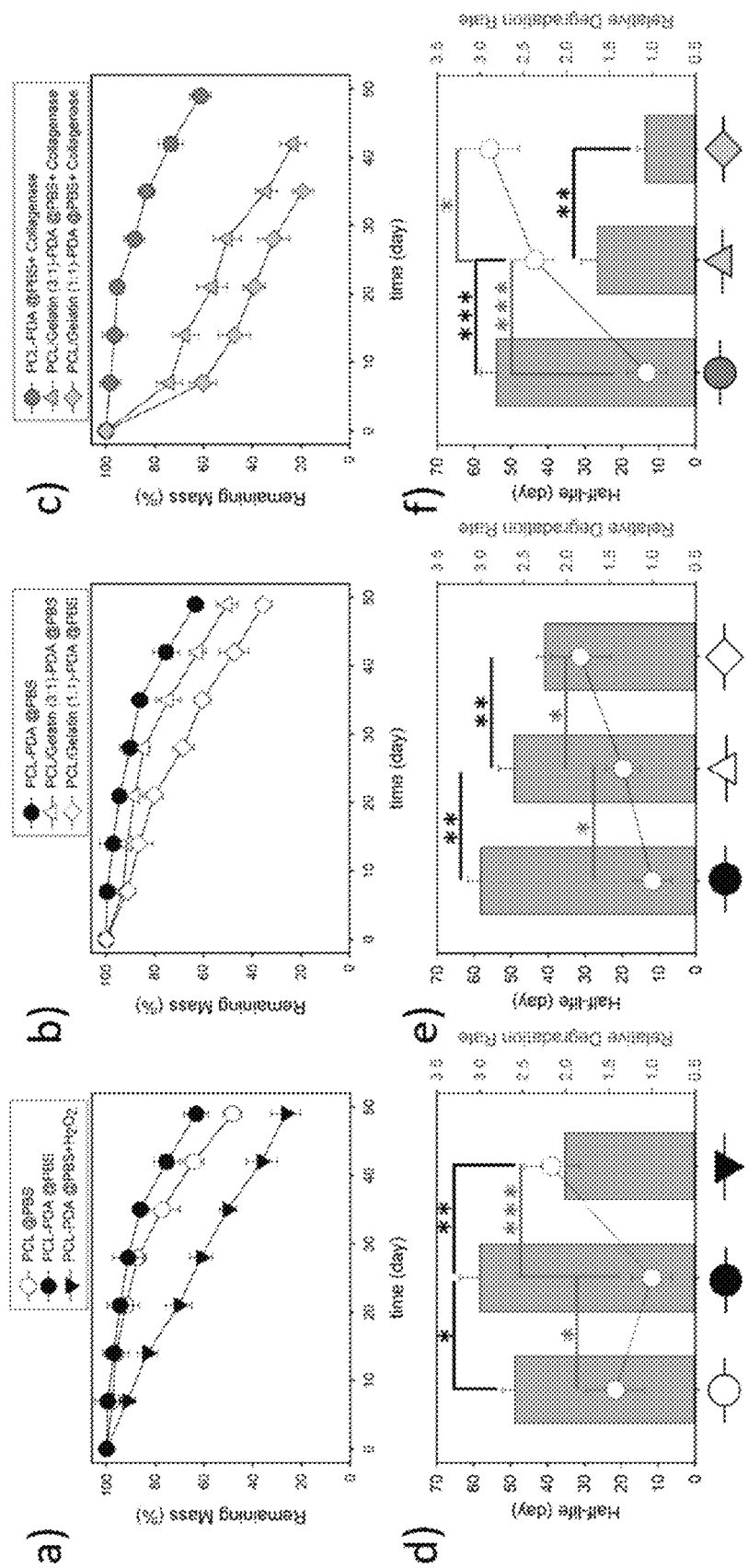
FIG. 2. In vitro degradation profiles of PCL and PCL-PDA-based membranes at 37° C. Values reported as % of original mass remaining (a) Effect of incubation condition in regular or oxidative media on degradation. (b) Degradation behavior can be altered by inclusion of gelatin biopolymer in the formulation as well as incubation of membrane in regular PBS (b) and collagenase-containing (c) solutions. Calculated degradation half-lives and degradation rates (relative to fastest degrading sample) are demonstrated in (d), (e), and (f). Data are expressed as average±SD. The results were statistically analyzed using unpaired t-tests, n=3. For all the tests, the threshold was set to $p<0.05$ for "statistically significant", $p<0.01$ for "statistically very significant" and $p<0.001$ for "statistically extremely significant". Statistical significance is indicated by * (significant),  (very significant) and * (extremely significant) for indicated comparisons.

The geometry optimization of the HA unit cell was carried out by making use of CASTEP code implemented in Matethickness of all three surfaces was set to be about 1.3 nm. Then, the surface areas of the cleaved HA surfaces were increased by periodic replication. FIG. 2 illustrates the constructed HA surfaces. Finally, all three surfaces were converted to periodic simulation cells by adding a vacuum space of thickness 4 nm above the surface.

Molecular Dynamics Simulation. MD simulations were done to examine and compare the adhesion propensities of PCL and PDA molecules over the HA substrates. These classical simulations were conducted under dry (i.e., gas phase or in vacuum) and wet (i.e., aqueous phase or in solution) conditions. For MD simulations in dry environments, the geometry-optimized PCL and PDA derived from QM calculations were placed over all HA surfaces. To conduct simulations in aqueous phase, a water layer of 600 $H_2O$ molecules was also inserted into the HA cells. The introduced water layer was considered to consist of lower and upper solvent sub-layers each containing approximately 300 $H_2O$ molecules. The water molecules forming the lower sub-layer dissolved the PCL (or PDA) molecule and were free to move above the HA surface. However, the position of solvents in the upper water sub-layer was constrained to behave as a rigid solvent wall for the lower layer.

The prepared simulation cells were then optimized by using Smart minimizer algorithm for 1000 steps, as available in Materials Studio software 11. Afterwards, MD simulations were conducted on energy-minimized cells, executed under the NVT ensemble for 250 ps at 298 K. All potential energy parameters required for bonded and non-bonded interactions were taken from COMPASS (condensed-phase optimized molecular potentials for atomistic simulation studies) force field, except the partial charges of PCL, PDA, and HA extracted from QM computations. The non-bonded van der Waals (vdW) and electrostatic (columbic) interactions were described by the Ewald scheme. In order to integrate the Newton's equation of motion, the velocity Verlet integrator with a time step of 1 fs was applied. Within dynamic NVT MD simulations, the temperature was monitored using an Andersen thermostat, and the positions of all HA atoms and water molecules in the upper solvent layer were kept constrained.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A biomimetic composition comprising:
a fibrous membrane patterned with niches, the membrane comprising:
a synthetic polymer; and
a coating comprising polydopamine disposed on said synthetic polymer, wherein the niches have a width of 50-700 micrometers and a depth of 10-100 micrometers, and wherein the niches comprise a pattern configured to facilitate adhesion of cells to the membrane.

2. The biomimetic composition of claim 1, wherein the composition further comprises at least one stem cell attractant disposed on the coating.

3. The composition of claim 2, wherein the at least one stem cell attractant comprises a cytokine.

4. The composition of claim 3, wherein the cytokine is SDF-1α.

5. The composition of claim 2, wherein the composition further comprises an additional stem cell attractant.

6. The composition of claim 5, wherein the additional stem cell attractant is a growth factor.

7. The composition of claim 6, wherein the growth factor comprises a bone morphogenetic growth factor, a vascular endothelial growth factor, or combination thereof.

8. The composition of claim 1, wherein the synthetic polymer comprises poly(ε-caprolactone) (PCL).

9. The composition of claim 1, wherein the niches comprise a pattern configured to facilitate adhesion of stem cells to the membrane.

10. The composition of claim 1, further comprising a gelatin protein disposed on the membrane.

11. The composition of claim 10, wherein the ratio of gelatin protein to the synthetic polymer is in a range of about 1:1 to about 1:4.

12. The composition of claim 1, wherein the pattern comprises a micropattern.

13. The composition of claim 12, wherein the micropattern comprises a morphological micropattern.

14. A process for preparing the biomimetic composition of claim 1, said process comprising:
depositing a synthetic polymer on a substrate to form a fibrous membrane;
patterning the fibrous membrane with niches; and
depositing a coating comprising polydopamine on the synthetic polymer.

15. A method of promoting periodontal tissue regeneration in a subject in need thereof, said method comprising:
positioning the biomimetic composition of claim 1 between a gum and a root surface of a tooth in the subject,
thereby promoting periodontal tissue regeneration in the subject.

* * * * *